United States Patent
Boettcher et al.

(10) Patent No.: US 11,129,874 B2
(45) Date of Patent: *Sep. 28, 2021

(54) NUCLEIC ACIDS ENCODING FGF21-FC FUSION PROTEINS

(71) Applicant: Novartis AG, Basel (CH)

(72) Inventors: Brian R. Boettcher, Winchester, MA (US); Shari Lynn Caplan, Lunenburg, MA (US); Douglas S. Daniels, Arlington, MA (US); Norio Hamamatsu, Belmont, MA (US); Stuart Licht, Cambridge, MA (US); Stephen Craig Weldon, Leominster, MA (US)

(73) Assignee: Novartis AG, Basel (CH)

(*) Notice: Subject to any disclaimer, the term of this patent is extended or adjusted under 35 U.S.C. 154(b) by 57 days.

This patent is subject to a terminal disclaimer.

(21) Appl. No.: 16/117,960

(22) Filed: Aug. 30, 2018

(65) Prior Publication Data

US 2018/0369332 A1 Dec. 27, 2018

Related U.S. Application Data

(60) Continuation of application No. 14/987,338, filed on Jan. 4, 2016, now Pat. No. 10,076,554, which is a division of application No. 14/630,206, filed on Feb. 24, 2015, now Pat. No. 9,266,935, which is a division of application No. 13/626,194, filed on Sep. 25, 2012, now Pat. No. 9,006,400.

(60) Provisional application No. 61/539,280, filed on Sep. 26, 2011.

(51) Int. Cl.
*C07K 14/50* (2006.01)
*A61K 38/18* (2006.01)
*A61K 45/06* (2006.01)
*A61K 38/00* (2006.01)

(52) U.S. Cl.
CPC .......... *A61K 38/1825* (2013.01); *A61K 45/06* (2013.01); *C07K 14/50* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,716,626 B1 | 4/2004 | Itoh et al. | |
| 7,576,190 B2 * | 8/2009 | Glaesner | C07K 14/50 530/399 |
| 9,023,791 B2 | 5/2015 | Boettcher et al. | |
| 2007/0237768 A1 * | 10/2007 | Glaesner | C07K 14/50 424/134.1 |
| 2010/0285131 A1 * | 11/2010 | Belouski | A61P 9/10 424/484 |
| 2012/0052069 A1 * | 3/2012 | Belouski | A61P 3/04 424/134.1 |
| 2013/0129724 A1 | 5/2013 | Boettcher et al. | |
| 2016/0051628 A1 | 2/2016 | Boettcher et al. | |
| 2017/0065678 A1 | 3/2017 | Diener et al. | |
| 2017/0166621 A1 | 6/2017 | Boettcher et al. | |

FOREIGN PATENT DOCUMENTS

| | | |
|---|---|---|
| WO | 2003/011213 A2 | 2/2003 |
| WO | 2006/078463 A2 | 7/2006 |
| WO | 2010/129503 A1 | 11/2010 |
| WO | 2010/129600 A2 | 11/2010 |
| WO | 2012/066075 A1 | 5/2012 |
| WO | 2013/049234 A2 | 4/2013 |
| WO | 2013/049247 A1 | 4/2013 |
| WO | 2015/138278 A1 | 9/2017 |

OTHER PUBLICATIONS

Kharitonenkov, et al., "FGF-21 as a novel metabolic regulator", Journal of Clinical Invest., 115(6):1627-35. (2005).

* cited by examiner

*Primary Examiner* — Christine J Saoud
(74) *Attorney, Agent, or Firm* — McNeill Baur PLLC

(57) ABSTRACT

The invention relates to nucleic acids encoding fusion proteins comprising polypeptide and protein variants of fibroblast growth factor 21 (FGF21) with improved pharmaceutical properties. Also disclosed are vectors and host cells comprising the same and methods of producing the fusion proteins.

12 Claims, 9 Drawing Sheets

Specification includes a Sequence Listing.

SEQUENCE LISTING

```
<160> NUMBER OF SEQ ID NOS: 13

<210> SEQ ID NO 1
<211> LENGTH: 209
<212> TYPE: PRT
<213> ORGANISM: Homo sapiens

<400> SEQUENCE: 1

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110
```

-continued

```
Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
        130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Ala Leu Pro Glu
                165                 170                 175

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Ala
                195                 200                 205

Ser
```

<210> SEQ ID NO 2
<211> LENGTH: 940
<212> TYPE: DNA
<213> ORGANISM: Homo sapiens

<400> SEQUENCE: 2

```
ctgtcagctg aggatccagc cgaaagagga gccaggcact caggccacct gagtctactc      60
acctggacaa ctggaatctg gcaccaattc taaaccactc agcttctccg agctcacacc     120
ccggagatca cctgaggacc cgagccattg atggactcgg acgagaccgg gttcgagcac     180
tcaggactgt gggtttctgt gctggctggt cttctgctgg agcctgcca ggcacacccc      240
atccctgact ccagtcctct cctgcaattc gggggcaag tccggcagcg gtacctctac      300
acagatgatg cccagcagac agaagcccac ctggagatca gggaggatgg acggtgggg      360
ggcgctgctg accagagccc cgaaagtctc ctgcagctga aagccttgaa gccgggagtt     420
attcaaatct gggagtcaa gacatccagg ttcctgtgcc agcggccaga tggggccctg      480
tatggatcgc tccactttga ccctgaggcc tgcagcttcc gggagctgct tcttgaggac     540
ggatacaatg tttaccagtc cgaagcccac ggcctcccgc tgcacctgcc agggaacaag     600
tccccacacc gggaccctgc accccgagga ccagctcgct tcctgccact accaggcctg     660
ccccccgcac tcccggagcc acccggaatc ctggccccccc agcccccga tgtgggctcc     720
tcggaccctc tgagcatggt gggaccttcc cagggccgaa gccccagcta cgcttcctga     780
agccagaggc tgtttactat gacatctcct ctttatttat taggttattt atcttatta     840
tttttttatt tttcttactt gagataataa agagttccag aggagaaaaa aaaaaaaaa     900
aaaaaaaaa aaaaaaaaa aaaaaaaaa aaaaaaaaa                               940
```

<210> SEQ ID NO 3
<211> LENGTH: 181
<212> TYPE: PRT
<213> ORGANISM: Homo sapiens

<400> SEQUENCE: 3

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60
```

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 4
<211> LENGTH: 546
<212> TYPE: DNA
<213> ORGANISM: Homo sapiens

<400> SEQUENCE: 4
caccccatcc ctgactccag tcctctcctg caattcgggg gccaagtccg gcagcggtac      60
ctctacacag atgatgccca gcagacagaa gcccacctgg agatcaggga ggatgggacg     120 gtgggggggcg ctgctgacca gagccccgaa agtctcctgc agctgaaagc cttgaagccg     180
ggagttattc aaatcttggg agtcaagaca tccaggttcc tgtgccagcg gccagatggg     240
gccctgtatg gatcgctcca ctttgaccct gaggcctgca gcttccggga gctgcttctt     300
gaggacggat acaatgttta ccagtccgaa gcccacggcc tcccgctgca cctgccaggg     360
aacaagtccc cacaccggga ccctgcaccc cgaggaccag ctcgcttcct gccactacca     420
ggcctgcccc ccgcactccc ggagccaccc ggaatcctgg ccccccagcc cccgatgtg     480 ggctcctcgg accctctgag catggtggga ccttcccagg gccgaagccc cagctacgct     540
tcctga                                                               546

<210> SEQ ID NO 5
<211> LENGTH: 28
<212> TYPE: PRT
<213> ORGANISM: Homo sapiens

<400> SEQUENCE: 5

Met Asp Ser Asp Glu Thr Gly Phe Glu His Ser Gly Leu Trp Val Ser
  1               5                  10                  15

Val Leu Ala Gly Leu Leu Leu Gly Ala Cys Gln Ala
             20                  25

<210> SEQ ID NO 6
<211> LENGTH: 15
<212> TYPE: DNA
<213> ORGANISM: Homo sapiens

<400> SEQUENCE: 6
ggggsggggs gggs                                                       15

<210> SEQ ID NO 7

<211> LENGTH: 406
<212> TYPE: PRT
<213> ORGANISM: Homo sapiens

<400> SEQUENCE: 7

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Ser Asp Ser Ser Pro Leu Leu Gln Phe Gly Gly Gln
225                 230                 235                 240

Val Arg Gln Arg Tyr Leu Tyr Thr Asp Ala Gln Gln Thr Glu Ala
                245                 250                 255

His Leu Glu Ile Arg Glu Asp Gly Thr Val Gly Gly Ala Ala Asp Gln
            260                 265                 270

Ser Pro Glu Ser Leu Leu Gln Leu Lys Ala Leu Lys Pro Gly Val Ile
        275                 280                 285

Gln Ile Leu Gly Val Lys Thr Ser Arg Phe Leu Cys Gln Arg Pro Asp
    290                 295                 300

Gly Ala Leu Tyr Gly Ser Leu His Phe Asp Pro Glu Ala Cys Ser Phe
305                 310                 315                 320

Arg Glu Leu Leu Leu Glu Asp Gly Tyr Asn Val Tyr Gln Ser Glu Ala
                325                 330                 335

His Gly Leu Pro Leu His Leu Pro Gly Asn Lys Ser Pro His Arg Asp
            340                 345                 350

Pro Ala Pro Arg Gly Pro Ala Arg Phe Leu Pro Leu Pro Gly Leu Pro
        355                 360                 365

Pro Ala Leu Pro Glu Pro Gly Ile Leu Ala Pro Gln Pro Pro Asp
    370                 375                 380

Val Gly Ser Ser Asp Pro Leu Ser Met Val Gly Pro Ser Gln Gly Arg
```

```
385                 390                 395                 400

Ser Pro Ser Tyr Ala Ser
                    405

<210> SEQ ID NO 8
<211> LENGTH: 419
<212> TYPE: PRT
<213> ORGANISM: Homo sapiens

<400> SEQUENCE: 8

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Gly Ser Gly Gly Gly
225                 230                 235                 240

Gly Ser Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Leu
                325                 330                 335

Leu Leu Glu Asp Gly Tyr Asn Val Tyr Gln Ser Glu Ala His Gly Leu
            340                 345                 350
```

```
Pro Leu His Leu Pro Gly Asn Lys Ser Pro His Arg Asp Pro Ala Pro
            355                 360                 365

Arg Gly Pro Ala Arg Phe Leu Pro Leu Pro Gly Leu Pro Pro Ala Leu
370                 375                 380

Pro Glu Pro Pro Gly Ile Leu Ala Pro Gln Pro Pro Asp Val Gly Ser
385                 390                 395                 400

Ser Asp Pro Leu Ser Met Val Gly Pro Ser Gln Gly Arg Ser Pro Ser
                405                 410                 415

Tyr Ala Ser

<210> SEQ ID NO 9
<211> LENGTH: 177
<212> TYPE: PRT
<213> ORGANISM: Homo sapiens

<400> SEQUENCE: 9

Asp Ser Ser Pro Leu Leu Gln Phe Gly Gly Gln Val Arg Gln Arg Tyr
1               5                   10                  15

Leu Tyr Thr Asp Asp Ala Gln Glu Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Glu Leu Lys Ala Leu Lys Pro Gly Val Ile Gln Ile Leu Gly Val
50                  55                  60

Lys Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asp Gly Tyr Asn Val Tyr Gln Ser Glu Ala His Gly Leu Pro Leu
            100                 105                 110

His Leu Pro Gly Asn Arg Ser Pro His Cys Asp Pro Ala Pro Gln Gly
        115                 120                 125

Pro Ala Arg Phe Leu Pro Leu Pro Gly Leu Pro Ala Leu Pro Glu
130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 10
<211> LENGTH: 406
<212> TYPE: PRT
<213> ORGANISM: Homo sapiens

<400> SEQUENCE: 10

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80
```

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Ser Asp Ser Ser Pro Leu Leu Gln Phe Gly Gly Gln
225                 230                 235                 240

Val Arg Gln Arg Tyr Leu Tyr Thr Asp Ala Cys Gln Thr Glu Ala
                245                 250                 255

His Leu Glu Ile Arg Glu Asp Gly Thr Val Gly Gly Ala Ala Asp Gln
            260                 265                 270

Ser Pro Glu Ser Leu Leu Gln Leu Lys Ala Leu Lys Pro Gly Val Ile
        275                 280                 285

Gln Ile Leu Gly Val Lys Thr Ser Arg Phe Leu Cys Gln Arg Pro Asp
    290                 295                 300

Gly Thr Leu Tyr Gly Ser Leu His Phe Asp Pro Glu Ala Cys Ser Phe
305                 310                 315                 320

Arg Glu Leu Leu Leu Glu Asp Gly Tyr Asn Val Tyr Gln Ser Glu Ala
                325                 330                 335

His Gly Leu Pro Leu His Leu Pro Cys Asn Arg Ser Pro His Arg Asp
            340                 345                 350

Pro Ala Ser Arg Gly Pro Ala Arg Phe Leu Pro Leu Pro Gly Leu Pro
        355                 360                 365

Pro Ala Leu Pro Glu Pro Gly Ile Leu Ala Pro Gln Pro Pro Asp
    370                 375                 380

Val Gly Ser Ser Asp Pro Leu Ala Met Val Gly Gly Ser Gln Ala Arg
385                 390                 395                 400

Ser Pro Ser Tyr Ala Ser
                405

<210> SEQ ID NO 11
<211> LENGTH: 406
<212> TYPE: PRT
<213> ORGANISM: Homo sapiens

<400> SEQUENCE: 11

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His

```
            35                  40                  45
Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys Gly Ser Asp Ser Ser Pro Leu Leu Gln Phe Gly Gly Gln
225                 230                 235                 240

Val Arg Gln Arg Tyr Leu Tyr Thr Asp Asp Ala Cys Gln Thr Glu Ala
                245                 250                 255

His Leu Glu Ile Arg Glu Asp Gly Thr Val Gly Gly Ala Ala Asp Gln
            260                 265                 270

Ser Pro Glu Ser Leu Leu Gln Leu Lys Ala Leu Lys Pro Gly Val Ile
        275                 280                 285

Gln Ile Leu Gly Val Lys Thr Ser Arg Phe Leu Cys Gln Lys Pro Asp
290                 295                 300

Gly Ala Leu Tyr Gly Ser Leu His Phe Asp Pro Glu Ala Cys Ser Phe
305                 310                 315                 320

Arg Glu Leu Leu Leu Glu Asp Gly Tyr Asn Val Tyr Gln Ser Glu Ala
                325                 330                 335

His Gly Leu Pro Leu His Leu Pro Cys Asn Arg Ser Pro His Arg Asp
            340                 345                 350

Pro Ala Ser Arg Gly Pro Ala Arg Phe Leu Pro Leu Pro Gly Leu Pro
        355                 360                 365

Pro Ala Leu Pro Glu Pro Gly Ile Leu Ala Pro Gln Pro Pro Asp
370                 375                 380

Val Gly Ser Ser Asp Pro Leu Ala Met Val Gly Gly Ser Gln Ala Arg
385                 390                 395                 400

Ser Pro Ser Tyr Ala Ser
                405

<210> SEQ ID NO 12
<211> LENGTH: 419
<212> TYPE: PRT
<213> ORGANISM: Homo sapiens

<400> SEQUENCE: 12
```

```
Asp Lys Thr His Thr Cys Pro Pro Cys Pro Ala Pro Glu Ala Ala Gly
 1               5                  10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Glu Glu Met Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys Gly Gly Gly Gly Ser Gly Gly Gly Gly Ser Gly Gly Gly
225                 230                 235                 240
Gly Ser Asp Ser Ser Pro Leu Leu Gln Phe Gly Gly Gln Val Arg Gln
                245                 250                 255
Arg Tyr Leu Tyr Thr Asp Asp Ala Cys Gln Thr Glu Ala His Leu Glu
            260                 265                 270
Ile Arg Glu Asp Gly Thr Val Gly Gly Ala Ala Asp Gln Ser Pro Glu
        275                 280                 285
Ser Leu Leu Gln Leu Lys Ala Leu Lys Pro Gly Val Ile Gln Ile Leu
    290                 295                 300
Gly Val Lys Thr Ser Arg Phe Leu Cys Gln Lys Pro Asp Gly Ala Leu
305                 310                 315                 320
Tyr Gly Ser Leu His Phe Asp Pro Glu Ala Cys Ser Phe Arg Glu Leu
                325                 330                 335
Leu Leu Glu Asp Gly Tyr Asn Val Tyr Gln Ser Glu Ala His Gly Leu
            340                 345                 350
Pro Leu His Leu Pro Cys Asn Arg Ser His Arg Asp Pro Ala Ser
        355                 360                 365
Arg Gly Pro Ala Arg Phe Leu Pro Leu Pro Gly Leu Pro Pro Ala Leu
    370                 375                 380
Pro Glu Pro Pro Gly Ile Leu Ala Pro Gln Pro Asp Val Gly Ser
385                 390                 395                 400
Ser Asp Pro Leu Ala Met Val Gly Gly Ser Gln Ala Arg Ser Pro Ser
                405                 410                 415
Tyr Ala Ser
```

<210> SEQ ID NO 13
<211> LENGTH: 419
<212> TYPE: PRT
<213> ORGANISM: Homo sapiens

<400> SEQUENCE: 13

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Ser Gly Gly Gly Gly
225                 230                 235                 240

Gly Ser Asp Ser Ser Pro Leu Leu Gln Phe Gly Gly Gln Val Arg Gln
                245                 250                 255

Arg Tyr Leu Tyr Thr Asp Asp Ala Cys Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Thr Leu
305                 310                 315                 320

Tyr Gly Ser Leu His Phe Asp Pro Glu Ala Cys Ser Phe Arg Glu Leu
                325                 330                 335

Leu Leu Glu Asp Gly Tyr Asn Val Tyr Gln Ser Glu Ala His Gly Leu
            340                 345                 350

Pro Leu His Leu Pro Cys Asn Arg Ser Pro His Arg Asp Pro Ala Ser
        355                 360                 365

Arg Gly Pro Ala Arg Phe Leu Pro Leu Pro Gly Leu Pro Pro Ala Leu
```

-continued

```
            370                 375                 380
Pro Glu Pro Pro Gly Ile Leu Ala Pro Gln Pro Pro Asp Val Gly Ser
385                 390                 395                 400

Ser Asp Pro Leu Ala Met Val Gly Gly Ser Gln Ala Arg Ser Pro Ser
                405                 410                 415

Tyr Ala Ser
```

NUCLEIC ACIDS ENCODING FGF21-FC FUSION PROTEINS

This application is a continuation of U.S. patent application Ser. No. 14/987,338, filed Jan. 4, 2016, which is a divisional application of U.S. patent application Ser. No. 14/630,206, filed Feb. 24, 2015, now U.S. Pat. No. 9,266,935, which is a divisional of U.S. patent application Ser. No. 13/626,194, filed Sep. 25, 2012, now U.S. Pat. No. 9,006,400, which claims priority to U.S. Provisional Application No. 61/539,280, filed Sep. 26, 2011, all of which are incorporated by reference in their entirety.

FIELD OF THE INVENTION

The present invention relates to new fusion proteins comprising fibroblast growth factor 21 (FGF21) known to improve metabolic profiles in subjects to whom they are administered.

BACKGROUND OF THE INVENTION

The fibroblast growth factor (FGF) family is characterized by 22 genetically distinct, homologous ligands, which are grouped into seven subfamilies. FGF-21 is most closely related to, and forms a subfamily with, FGF-19 and FGF-23. This FGF subfamily regulates diverse physiological processes uncommon to classical FGFs, namely energy and bile acid homeostasis, glucose and lipid metabolism, and phosphate as well as vitamin D homeostasis. Moreover, unlike other FGFs, this subfamily acts in an endocrine fashion. (Moore, D. D. (2007) Science 316, 1436-8)(Beenken et al. (2009) Nature Reviews Drug Discovery 8, 235).

FGF21 is a 209 amino acid polypeptide containing a 28 amino acid leader sequence (SEQ ID NO:5). Human FGF21 has about 79% amino acid identity to mouse FGF21 and about 80% amino acid identity to rat FGF21. Fibroblast growth factor 21 (FGF21) has been described as a treatment for ischemic vascular disease, wound healing, and diseases associated with loss of pulmonary, bronchia or alveolar cell function. (Nishimura et al. (2000) Biochimica et Biophysica Acta, 1492:203-206; patent publication WO01/36640; and patent publication WO01/18172) Although FGF-21 activates FGF receptors and downstream signaling molecules, including FRS2a and ERK, direct interaction of FGFRs and FGF-21 has not been detected. Studies have identified β-klotho, which is highly expressed in liver, adipocytes and pancreas, as a determinant of the cellular response to FGF-21 and a cofactor which mediates FGF-21 signaling through FGFRs (Kurosu, H. et al. (2007) J Biol Chem 282, 26687-95). FGF21 is a potent agonist of the FGFR1(IIIc), FGFR2 (IIIc) and FGFR3(IIIc) β-klotho signaling complexes.

FGF-21 has been shown to induce insulin-independent glucose uptake. FGF-21 has also been shown to ameliorate hyperglycemia in a range of diabetic rodent models. In addition, transgenic mice over-expressing FGF-21 were found to be resistant to diet-induced metabolic abnormalities, and demonstrated decreased body weight and fat mass, and enhancements in insulin sensitivity (Badman, M. K. et al. (2007) Cell Metab 5, 426-37). Administration of FGF-21 to diabetic non-human primates caused a decline in fasting plasma glucose, triglycerides, insulin and glucagon levels, and led to significant improvements in lipoprotein profiles including a nearly 80% increase in HDL cholesterol (Kharitonenkov, A. et al. (2007) Endocrinology 148, 774-81). Recent studies investigating the molecular mechanisms of FGF21 action have identified FGF21 as an important endocrine hormone that helps to control adaptation to the fasting state. (Badman et al. (2009) Endocrinology 150, 4931) (Inagaki et al. (2007) Cell Metabolism 5, 415) This provides a previously missing link downstream of PPARα, by which the liver communicates with the rest of the body in regulating the biology of energy homeostasis. (Galman et al. (2008) Cell Metabolism 8, 169)(Lundasen et al. (2007) Biochemical and Biophysical Research Communications 360, 437).

FGF21 regulates adipocyte homeostasis through activation of an AMPK/SIRT1/PGC1α pathway to inhibit PPARγ expression and increase mitochondrial function. (Chau et al. (2010) PNAS 107, 12553) FGF21 also increases glucose uptake by skeletal muscle as measured in cultured human myotubes and isolated mouse tissue. FGF21 treatment of rodent islet cells leads to improved function and survival through activation of ERK½ and Akt pathways. (Wente et al. (2006) Diabetes 55, 2470) FGF21 treatment also results in altered gene expression for lipogenesis and fatty acid oxidation enzymes in rodent livers, likely through HNF4α and Foxa2 signaling.

A difficulty associated with using FGF-21 directly as a biotherapeutic is that its half-life is very short. (Kharitonenkov, A. et al. (2005) Journal of Clinical Investigation 115: 1627-1635) In mice, the half-life of human FGF21 is 0.5 to 1 hours, and in cynomolgus monkeys, the half-life is 2 to 3 hours. FGF21 may be utilized as a multi-use, sterile pharmaceutical formulation. However, it has been determined that preservatives, i.e., m-cresol, have an adverse affect on its stability under these conditions.

In developing an FGF21 protein for use as a therapeutic in the treatment of type 1 and type 2 diabetes mellitus and other metabolic conditions, an increase in half-life and stability would be desirable. FGF21 proteins having enhanced half-life and stability would allow for less frequent dosing of patients being administered the protein. Clearly, there is a need to develop a stable aqueous protein formulation for the therapeutic protein FGF21.

Furthermore, significant challenge in the development of FGF21 as a protein pharmaceuticals, is to cope with its physical and chemical instabilities. The compositional variety and characteristics of proteins define specific behaviors such as folding, conformational stability, and unfolding/ denaturation. Such characteristics should be addressed when aiming to stabilize proteins in the course of developing pharmaceutical formulation conditions utilizing aqueous protein solutions (Wang, W., Int. J. of Pharmaceutics, 18, (1999)). A desired effect of stabilizing therapeutic proteins of interest, e.g., the proteins of the present invention, is increasing resistance to proteolysis and enzymatic degradation, thereby improving protein stability and reducing protein aggregation.

SUMMARY OF THE INVENTION

The invention relates to the identification of new fusion proteins which comprise fibroblast growth factor 21 (FGF21) and which have improved pharmaceutical properties over the wild-type FGF21 and variants thereof under pharmaceutical formulation conditions, e.g., are more stable, possess the ability to improve metabolic parameters for subjects to whom they are administered, are less susceptible to proteolysis and enzymatic degradation, and are less likely to aggregate and form complexes. The fusion proteins of the invention comprise truncations, mutations, and variants of FGF21.

Also disclosed are methods for treating FGF21-associated disorders, as well as other metabolic, endocrine, and cardiovascular disorders, such as obesity, type 1 and type 2 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, metabolic syndrome, acute myocardial infarction, hypertension, cardiovascular disease, atherosclerosis, peripheral arterial disease, stroke, heart failure, coronary heart disease, kidney disease, diabetic complications, neuropathy, gastroparesis, disorders associated with severe inactivating mutations in the insulin receptor, and other metabolic disorders, and in reducing the mortality and morbidity of critically ill patients.

The fusion proteins of the present invention may be used as a once weekly injectable either alone or in combination with oral anti-diabetic agents which will improve the glycemic control, body weight and lipid profile of type 1 and type 2 diabetes mellitus patients. The proteins may also be used for the treatment of obesity or other FGF21-associated conditions.

The fusion proteins of the invention overcome the significant hurdles of physical instabilities associated with protein therapeutics, including, for instance, with the administration of the wild-type FGF21, by presenting proteins which are more stable, less susceptible to proteolysis and enzymatic degradation, and less likely to aggregate and form complexes, than wild-type FGF21 under pharmaceutical formulation conditions.

In a first aspect, the invention provides Fibroblast Growth Factor 21 (FGF21) fusion proteins comprising one or more of the sequences listed in Table 1, and further described herein. The FGF21 sequences listed in Table 1 may be variants of the wild-type FGF21 sequence, e.g., the wild-type FGF21 sequence with NCBI reference number NP_061986.1, and found in such issued patents as, e.g., U.S. Pat. No. 6,716,626B1, assigned to Chiron Corporation.

Said fusions may be, for example, between the variant FGF21 sequences, e.g., the sequences of Table 1, and other molecules (a non-FGF21 portion), e.g., an IgG constant domain or fragment thereof (e.g., the Fc region), Human Serum Albumin (HSA), or albumin-binding polypeptides. In a preferred embodiment, the non-FGF21 portion of the molecule is an Fc region.

Other embodiments are drawn to polynucleotides encoding the fusion proteins of the invention, a vector containing said polynucleotides and a host cell carrying said vector.

Provided herein are methods used to generate the fusion proteins of the invention, wherein such methods involve modification of the wild-type FGF21 protein, via e.g., the site-specific incorporation of amino acids at positions of interest within the wild-type FGF21 protein, as well as the fusion between the FGF21 portion of the molecule to other molecules, e.g., an IgG constant domain or fragment thereof (e.g., the Fc region), Human Serum Albumin (HSA), or albumin-binding polypeptides. Said modifications and fusions enhance the biological properties of the fusion proteins of the invention relative to the wild-type versions of the proteins as well as, in some cases, serving as points of attachment for, e.g., labels and protein half-life extension agents, and for purposes of affixing said variants to the surface of a solid support. Related embodiments of the invention are methods to produce cells capable of producing said proteins of the invention, and of producing vectors containing DNA encoding said variants and fusions.

In various embodiments, the fusion proteins of the invention disclosed herein can comprise one or more fragments of the FGF21 wild-type sequences, including fragments as small as 8-12 amino acid residues in length, and wherein the polypeptide is capable of lowering blood glucose in a mammal. In various embodiments, the fusion proteins of the invention disclosed herein can comprise one or more variant of the FGF21 wild-type sequences, e.g., with one or more amino acid deletion, insertion, addition, or substitution relative to the wild-type sequences thereof.

In some embodiments, the fusion proteins of the invention disclosed herein can be covalently linked to one or more polymers, such as polyethylene glycol (PEG) or polysialic acid, whether at the position of site-specific amino acid modifications made relative to the wild-type FGF21, or at the position of amino acids commonly shared with the wild-type versions of those proteins. The PEG group is attached in such a way so as enhance, and/or not to interfere with, the biological function of the constituent portions of the fusion proteins of the invention, e.g., the FGF21 protein variants. In other embodiments, the polypeptides of the invention can be fused to a heterologous amino acid sequence, optionally via a linker, such as GS, GGGGSGGGGSGGGGS (SEQ ID NO:6). The heterologous amino acid sequence can be an IgG constant domain or fragment thereof (e.g., the Fc region), Human Serum Albumin (HSA), or albumin-binding polypeptides. Such fusion proteins disclosed herein can also form multimers.

In some embodiments, a heterologous amino acid sequence (e.g., HSA, Fc, etc.) is fused to the amino-terminal of the fusion proteins of the invention. In other embodiments, the fusion heterologous amino acid sequence (e.g., HSA, Fc, etc.) is fused to the carboxyl-terminal of the fusion proteins of the invention.

Yet another embodiment is drawn to methods of treating a patient exhibiting one or more FGF21-associated disorders, such as obesity, type 2 diabetes mellitus, type 1 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, metabolic syndrome, acute myocardial infarction, hypertension, cardiovascular disease, atherosclerosis, peripheral arterial disease, stroke, heart failure, coronary heart disease, kidney disease, diabetic complications, neuropathy, gastroparesis, disorders associated with inactivating mutations in the insulin receptor, and other metabolic disorders, comprising administering to said patient in need of such treatment a therapeutically effective amount of one or more proteins of the invention or a pharmaceutical composition thereof.

The invention also provides pharmaceutical compositions comprising the fusion proteins of the invention disclosed herein and a pharmaceutically acceptable formulation agent. Such pharmaceutical compositions can be used in a method for treating a metabolic disorder, and the method comprises administering to a human patient in need thereof a pharmaceutical composition of the invention. Non-limiting examples of metabolic disorders that can be treated include type 1 and type 2 diabetes mellitus and obesity.

These and other aspects of the invention will be elucidated in the following detailed description of the invention.

BRIEF DESCRIPTION OF THE DRAWINGS

FIG. 1A shows fed plasma glucose as a readout (circles represent vehicle (PBS—phosphate buffered saline), squares represent V76 at 5 mpk, and triangles represent V188 at 1 mpk. FIG. 1B shows fed plasma insulin as a readout (from left to right: vehicle, V76 at 5 mpk, and V188 at 1 mpk). FIG. 1C shows body weight as a readout (from left to right: vehicle, V76 at 5 mpk, and V188 at 1 mpk). FIG. 1D shows liver lipid content as a readout (from left to right: vehicle, V76 at 5 mpk, and V188 at 1 mpk).

FIG. 2A shows fed plasma glucose as a readout (circles represent vehicle (PBS—phosphate buffered saline), squares represent V76 at 5 mpk, and triangles represent V101 at 1 mpk. FIG. 2B shows fed plasma insulin as a readout (from left to right: vehicle, V76 at 5 mpk, and V101 at 1 mpk). FIG. 2C shows body weight as a readout (from left to right: vehicle, V76 at 5 mpk, and V101 at 1 mpk). FIG. 2D shows liver lipid content as a readout (from left to right: vehicle, V76 at 5 mpk, and V101 at 1 mpk).

FIG. 3A shows fed plasma glucose as a readout (circles represent vehicle (PBS—phosphate buffered saline), squares represent V76 at 5 mpk, and triangles represent V103 at 1 mpk. FIG. 3B shows fed plasma insulin as a readout (from left to right: vehicle, V76 at 5 mpk, and V103 at 1 mpk). FIG. 3C shows body weight as a readout (from left to right: vehicle, V76 at 5 mpk, and V103 at 1 mpk). FIG. 3D shows liver lipid content as a readout (from left to right: vehicle, V76 at 5 mpk, and V103 at 1 mpk).

FIG. 4A shows the plasma concentrations of fusion proteins of the invention in PCT Publication WO10/129600 described as Fc-L (15)-FGF21 (L98R, P171G) and Fc-L (15)-FGF21 (L98R, P171G, A180E), following the IV injection of said fusion in mice. FIG. 4B shows pharmacokinetic properties of the fusion proteins of the invention (V101, V103 & V188) after a single IV dose in the mouse as assayed by anti-Fc-ELISA compared with pharmacokinetic data generated in the mouse for V76 in a previous study using an anti-FGF21 antibody ELISA. FIG. 4C shows a spot check of the fusion proteins of the invention in an anti-FGF21 Western blot, consistent with anti-Fc-ELISA data at 120 hours and 15 days. The samples in the blot are as follows: A represents V101, B represents V103, and C represents V188. Control is V101 and serum. FIG. 4D demonstrates the significantly increased thermodynamic stability of the fusion proteins of the invention compared to V76. From top to bottom, the figure represents V101, V103, and V188, all of which have improved melting temperatures ($T_m$) compared to V76 ($T_m<50°$ C. (not shown)) and wild-type FGF21 ($T_m=46.5°$ C.±0.3 (not shown)).

DETAILED DESCRIPTION OF THE INVENTION

Figure 1A:
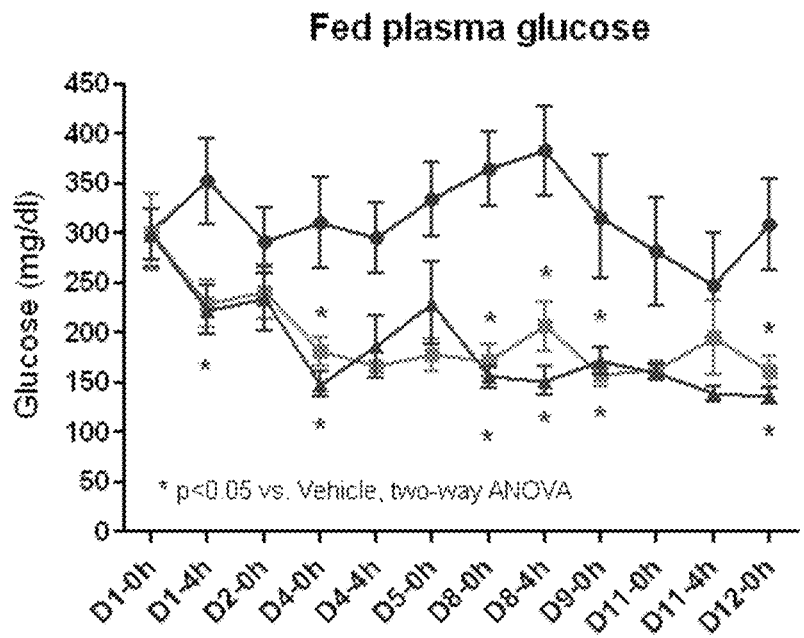
FIGS. 1A-1D show V188 has improved efficacy in the ob/ob diabetic mouse model over V76. V188 shows superior results when administered at 1 milligram per kilogram (mpk), compared to the 5 milligram per kilogram at which V76 was administered.
Figure 1B:
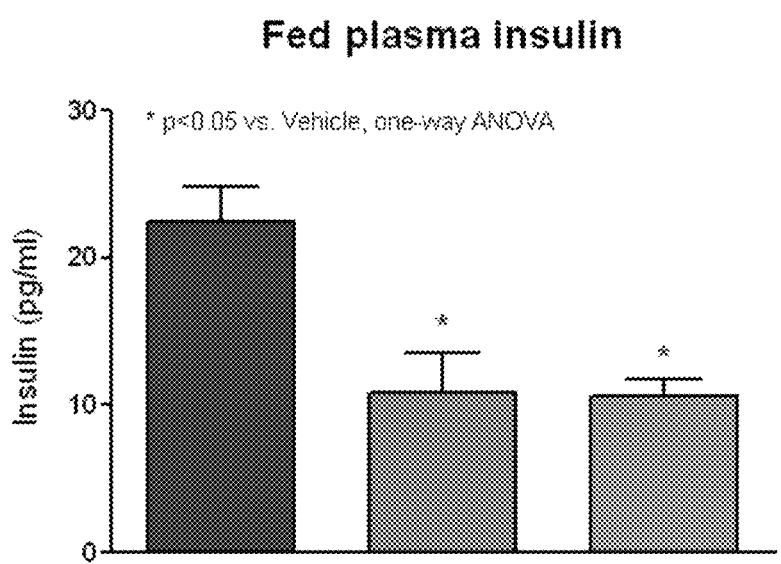
Figure 1C:
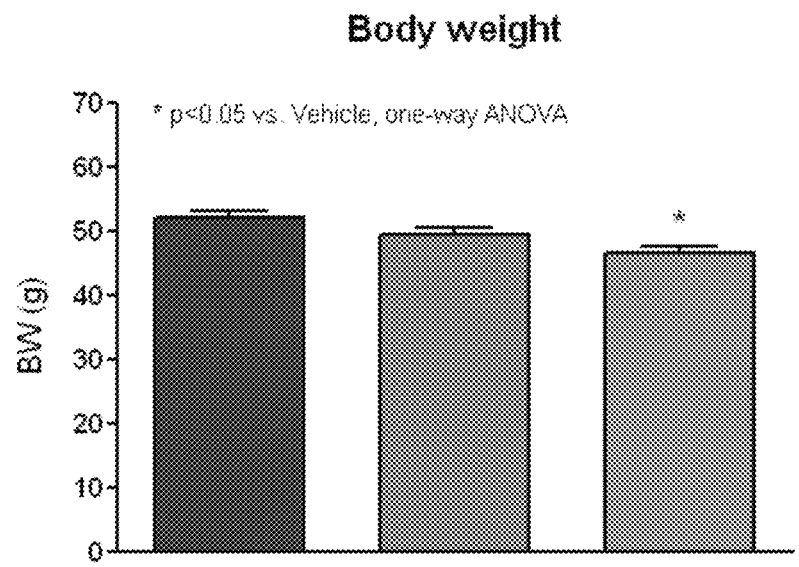
Figure 1D:
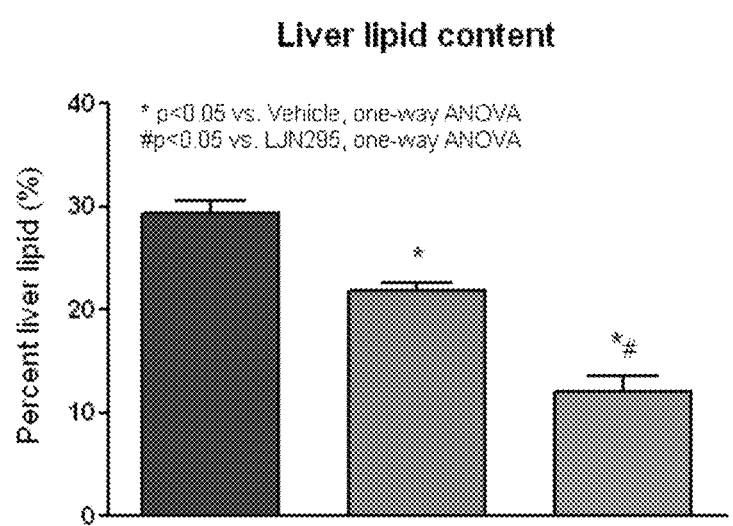
Figure 2A:
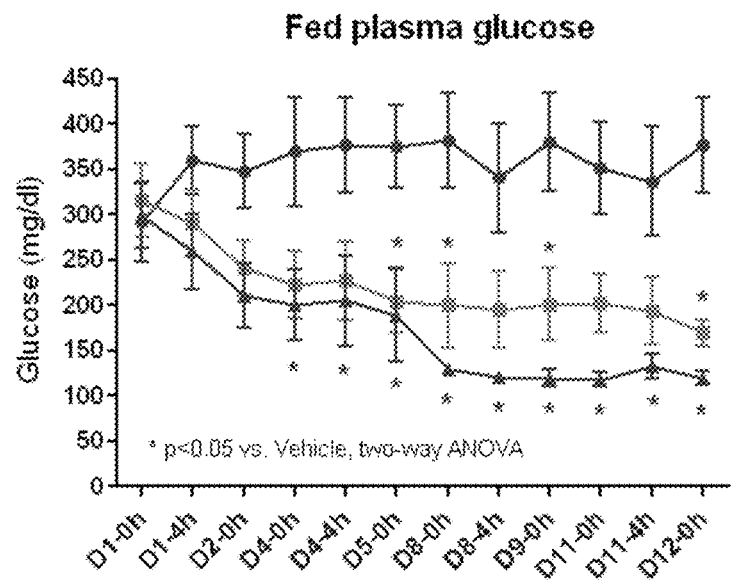
FIGS. 2A-2D show V101 has improved efficacy in the ob/ob diabetic mouse model over V76. V101 shows superior results when administered at 1 milligram per kilogram (mpk), compared to the 5 milligram per kilogram at which V76 was administered.
Figure 2B:
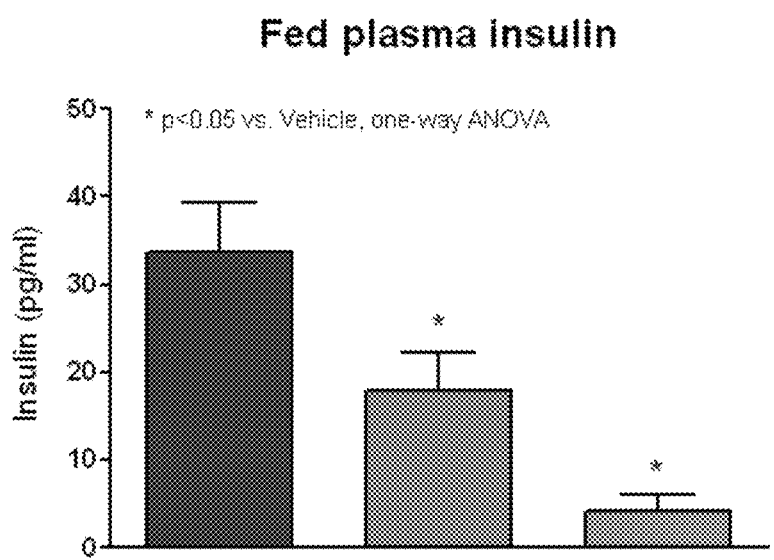
Figure 2C:
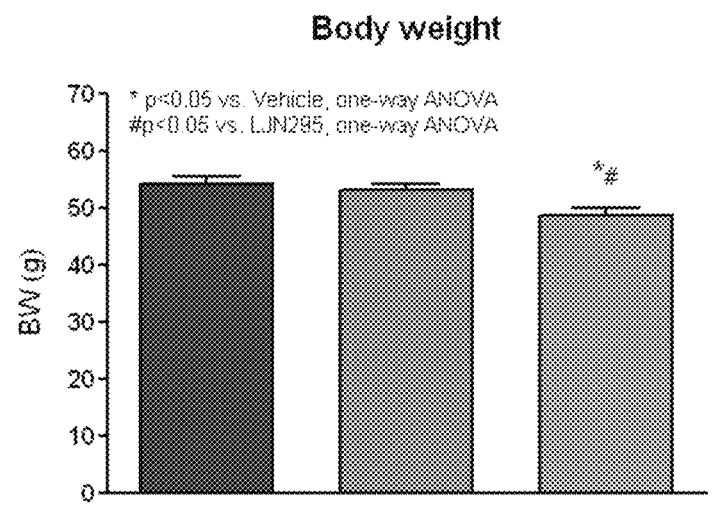
Figure 2D:
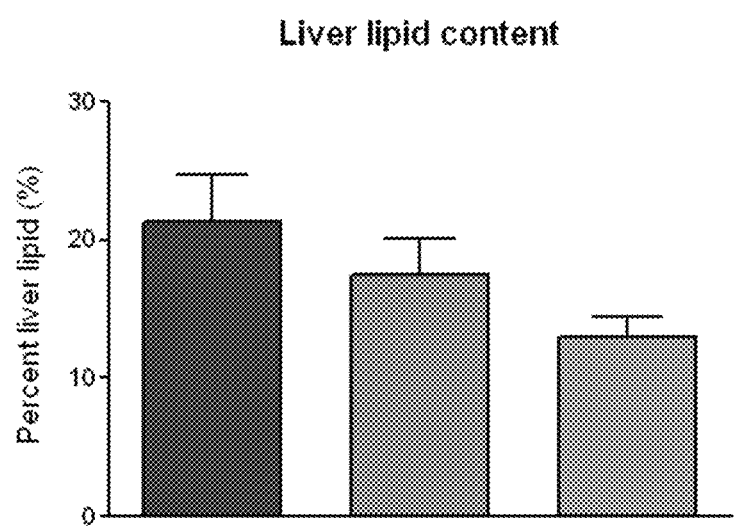
Figure 3A:
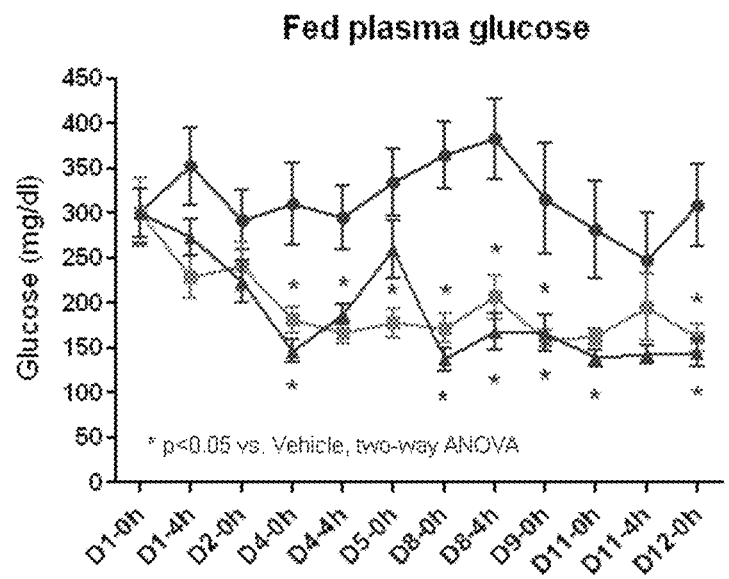
FIGS. 3A-3D show V103 has improved efficacy in the ob/ob diabetic mouse model over V76. V103 shows superior results when administered at 1 milligram per kilogram (mpk), compared to the 5 milligram per kilogram at which V76 was administered.
Figure 3B:
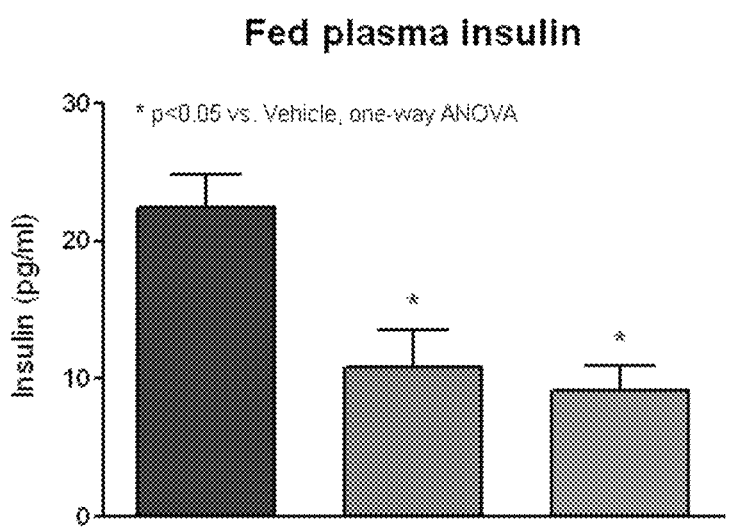
Figure 3C:
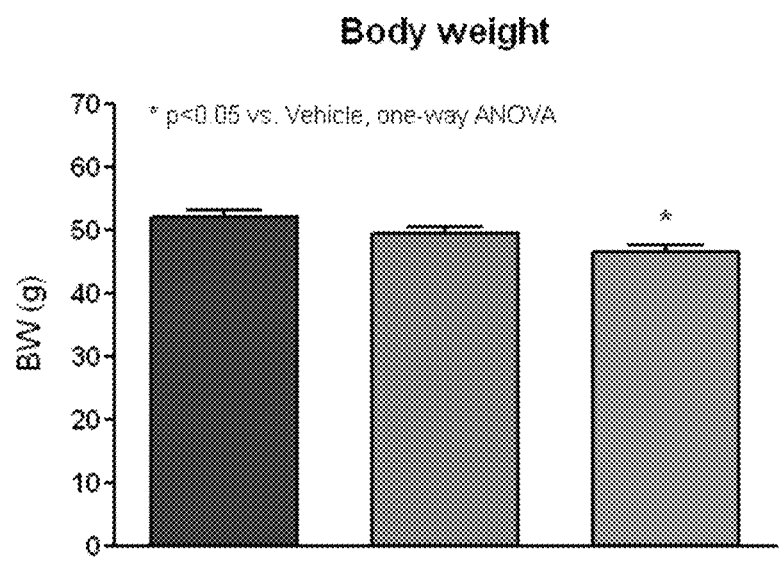
Figure 3D:
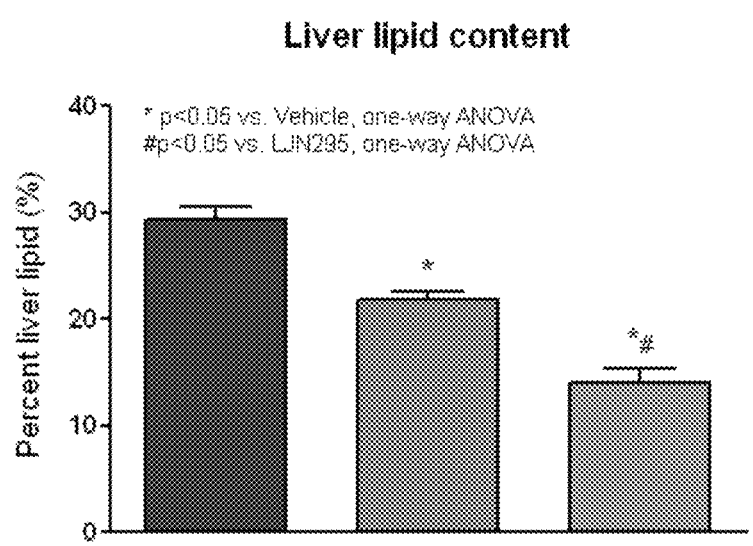

The fusion proteins of the present invention represent modified versions of the full length, wild-type FGF21 polypeptide, as known in the art. FGF21 wild-type sequence will serve as a reference sequence (SEQ ID NO:1), for instance, when comparisons between the FGF21 wild-type sequence and the protein variants are necessary. The FGF21 wild-type sequence has NCBI reference sequence number NP_061986.1, and can be found in such issued patents as, e.g., U.S. Pat. No. 6,716,626B1, assigned to Chiron Corporation (SEQ ID NO:1).

```
Met Asp Ser Asp Glu Thr Gly Phe Glu His Ser Gly Leu Trp Val Ser
 1               5                  10                  15

Val Leu Ala Gly Leu Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
                35                  40                  45

Leu Tyr Thr Asp Asp Ala Gln Gln Thr Glu Ala His Leu Glu Ile Arg
         50                  55                  60

Glu Asp Gly Thr Val Gly Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
                115                 120                 125

Glu Asp Gly Tyr Asn Val Tyr Gln Ser Glu Ala His Gly Leu Pro Leu
         130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175
```

```
Pro Pro Gly Ile Leu Ala Pro Gln Pro Pro Asp Val Gly Ser Ser Asp
        180                 185                 190

Pro Leu Ser Met Val Gly Pro Ser Gln Gly Arg Ser Pro Ser Tyr Ala
        195                 200                 205

Ser
209
```

The corresponding mRNA sequence coding for the full-length FGF21 polypeptide (NCBI reference sequence number NM_019113.2) is shown below (SEQ ID NO:2)

```
  1  ctgtcagctg aggatccagc cgaaagagga gccaggcact
     caggccacct gagtctactc
 61  acctggacaa ctggaatctg gcaccaattc taaaccactc
     agcttctccg agctcacacc
121  ccggagatca cctgaggacc cgagccattg atggactcgg
     acgagaccgg gttcgagcac
181  tcaggactgt gggtttctgt gctggctggt cttctgctgg
     gagcctgcca ggcacacccc
241  atccctgact ccagtcctct cctgcaattc gggggccaag
     tccggcagcg gtacctctac
301  acagatgatg cccagcagac agaagcccac ctggagatca
     gggaggatgg gacggtgggg
361  ggcgctgctg accagagccc cgaaagtctc ctgcagctga
     aagccttgaa gccgggagtt
421  attcaaatct tgggagtcaa gacatccagg ttcctgtgcc
     agcggccaga tggggccctg
481  tatggatcgc tccactttga ccctgaggcc tgcagcttcc
     gggagctgct tcttgaggac
541  ggatacaatg tttaccagtc cgaagcccac ggcctcccgc
     tgcacctgcc agggaacaag
601  tccccacacc gggaccctgc accccgagga ccagctcgct
     tcctgccact accaggcctg
661  cccccgcac tccggagcc acccggaatc ctggcccccc
     agccccccga tgtgggctcc
721  tcggaccctc tgagcatggt gggaccttcc cagggccgaa
     gccccagcta cgcttcctga
781  agccagaggc tgtttactat gacatctcct ctttatttat
     taggttattt atcttattta
841  tttttttatt tttcttactt gagataataa agagttccag
     aggagaaaaa aaaaaaaaaa
901  aaaaaaaaaa aaaaaaaaaa aaaaaaaaaa aaaaaaaaa
```

The mature FGF21 sequence lacks a leader sequence and may also include other modifications of a polypeptide such as proteolytic processing of the amino terminus (with or without a leader sequence) and/or the carboxyl terminus, cleavage of a smaller polypeptide from a larger precursor, N-linked and/or O-linked glycosylation, and other post-translational modifications understood by those with skill in the art. A representative example of a mature FGF21 sequence has the following sequence (SEQ ID NO:3, which represents amino acid positions 29-209 of full length FGF21 protein sequence (NCBI reference sequence number NP_061986.1)):

```
His Pro Ile Pro Asp Ser Ser Pro Leu Leu Gln Phe Gly Gly Gln Val
                5                  10                  15
Arg Gln Arg Tyr Leu Tyr Thr Asp Asp Ala Gln Gln Thr Glu Ala His
           20                  25                  30
Leu Glu Ile Arg Glu Asp Gly Thr Val Gly Gly Ala Ala Asp Gln Ser
       35                  40                  45
Pro Glu Ser Leu Leu Gln Leu Lys Ala Leu Lys Pro Gly Val Ile Gln
   50                  55                  60
Ile Leu Gly Val Lys Thr Ser Arg Phe Leu Cys Gln Arg Pro Asp Gly
65                  70                  75                  80
Ala Leu Tyr Gly Ser Leu His Phe Asp Pro Glu Ala Cys Ser Phe Arg
               85                  90                  95
Glu Leu Leu Leu Glu Asp Gly Tyr Asn Val Tyr Gln Ser Glu Ala His
                   100                 105                 110
Gly Leu Pro Leu His Leu Pro Gly Asn Lys Ser Pro His Arg Asp Pro
               115                 120                 125
Ala Pro Arg Gly Pro Ala Arg Phe Leu Pro Leu Pro Gly Leu Pro Pro
           130                 135                 140
```

```
Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

The corresponding cDNA sequence coding for the mature FGF21 polypeptide (SEQ ID NO:3) is shown below (SEQ ID NO:4):

```
  1  cacccatcc ctgactccag tcctctcctg caattcgggg
     gccaagtccg gcagcggtac
 61  ctctacacag atgatgccca gcagacagaa gcccacctgg
     agatcaggga ggatgggacg
121  gtgggggcg ctgctgacca gagccccgaa agtctcctgc
     agctgaaagc cttgaagccg
181  ggagttattc aaatcttggg agtcaagaca tccaggttcc
     tgtgccagcg gccagatggg
240  gccctgtatg gatcgctcca ctttgaccct gaggcctgca
     gcttccggga gctgcttctt
301  gaggacggat acaatgttta ccagtccgaa gcccacggcc
     tcccgctgca cctgccaggg
360  aacaagtccc cacaccggga ccctgcaccc cgaggaccag
     ctcgcttcct gccactacca
```

```
421  ggcctgcccc ccgcactccc ggagccaccc ggaatcctgg
     ccccccagcc ccccgatgtg
481  ggctcctcgg accctctgag catggtggga ccttcccagg
     gccgaagccc cagctacgct
541  tcctga
```

The fusion proteins of the invention may comprise protein variants or mutants of the wild-type proteins listed herein, e.g., FGF21 variants. As used herein, the terms "protein variant," "human variant," "polypeptide or protein variant," "variant," "mutant," as well as any like terms or specific versions thereof (e.g., "FGF21 protein variant," "variant," "FGF21 mutant," etc.) define protein or polypeptide sequences that comprise modifications, truncations, other variants of naturally occurring (i.e., wild-type) protein or polypeptide counterparts or corresponding native sequences. "Variant FGF21" or "FGF21 mutant," for instance, is described relative to the wild-type (i.e., naturally occurring) FGF21 protein as described herein.

Representative fusion protein sequences of the invention are listed in Table 1. The descriptions of said fusions include the FGF21 variant and, where applicable, a linker. The changes or substitutions employed by the FGF21 variant are numbered and described relative to wild-type FGF21. By way of example, "Variant 101 (V101)" (SEQ ID NO:10) is an Fc-FGF21 fusion with a two amino acid linker and the following substitutions made relative to wild type FGF21: Q55C, A109T, G148C, K150R, P158S, P174L, S195A, P199G, G202A.

TABLE 1

FGF21 Variant Fc fusion proteins

| SEQ ID NO: | Sequence | Name* |
|---|---|---|
| 7 | DKTHTCPPCP APEAAGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG<u>GS</u>D SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH RDPAPRGPAR FLPLPGLPPA LPEPPGILAP QPPDVGSSDP LSMVGPSQGR SPSYAS | Full Length N-term Fc-Fusion with 2 AA Linker (GS) and WI FGF21 |
| 8 | DKTHTCPPCP APEAAGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE | Full Length N-term Fc-Fusion with 15 AA Linker (GGGGS x 3) between Fc and WT FGF21 |

TABLE 1-continued

FGF21 Variant Fc fusion proteins

| SEQ ID NO: | Sequence | Name* |
|---|---|---|
| | ALHNHYTQKS LSLSPGKGGG GSGGGGSGGG GSDSSPLLQF GGQVRQRYLY TDDAQQTEAH LEIREDGTVG GAADQSPESL LQLKALKPGV IQILGVKTSR FLCQRPDGAL YGSLHFDPEA CSFRELLLED GYNVYQSEAH GLPLHLPGNK SPHRDPAPRG RARFLPLPGL PPALPEPPGI LAPQPPDVGS SDPLSMVGPS QGRSPSYAS | |
| 9 | DSSPLLQFGG QVRQRYLYTD DAQETEAHLE IREDGTVGGA AHQSPESLLE LKALKPGVIQ ILGVKTSRFL CQKPDGALYG SLHFDPEACS FRELLLEDGY NVYQSEAHGL PLHLPGNRSP HCDPAPQGPA RFLPLPGLPP ALPEPPGILA PQPPDVGSSD PLAMVGPSQG RSPSYAS | Variant #76 = Protein with 9 total mutations relative to wild-type FGF21 (as in WO01/018172) |
| 10 | DKTHTCPPCP APEAAGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGKGSD SSPLLQFGGQ VRQRYLYTDD ACQTEAHLEI REDGTVGGAA DQSPESLLQL KALKPGVIQI LGVKTSRFLC QRPDGTLYGS LHFDPEACSF RELLLEDGYN VYQSEAHGLP LHLPCNRSPH RDPASRGPAR FLPLPGLPPA LPEPPGILAP QPPDVGSSDP LAMVGGSQAR SPSYAS | Variant # 101 = N-term Fc Fusion with the 2 AA linker (GS) between Fc and FGF21 = (Q55C, A109T, G148C, K150R, P158S, S195A, P199G, G202A) |
| 11 | DKTHTCPPCP APEAAGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGKGSD SSPLLQFGGQ VRQRYLYTDD ACQTEAHLEI REDGTVGGAA DQSPESLLQL KALKPGVIQI LGVKTSRFLC QKPDGALYGS LHFDPEACSF RELLLEDGYN VYQSEAHGLP LHLPCNRSPH RDPASRGPAR FLPLPGLPPA LPEPPGILAP QPPDVGSSDP LAMVGGSQAR SPSYAS | Variant # 103 = N-term Fc Fusion with the 2 AA linker (GS) = (Q55C, R105K, G148C, K150R, P158S, S195A, P199G, G202A) |
| 12 | DKTHTCPPCP APEAAGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGKGGG GSGGGGSGGG GSDSSPLLQF GGQVRQRYLY TDDACQTEAH LEIREDGTVG GAADQSPESL LQLKALKPGV IQILGVKTSR FLCQKPDGAL YGSLHFDPEA CSFRELLLED GYNVYQSEAH GLPLHLPCNR SPHRDPASRG PARFLPLPGL PPALPEPPGI LAPQPPDVGS SDPLAMVGGS QARSPSYAS | Variant #188 = V103 with 15 AA Linker (GGGGS x 3) between Fc and FGF21 = (Q55C, R105K, G148C, K150R, P158S, S195A, P199G, G202A) |
| 13 | DKTHTCPPCP APEAAGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGKGGG GSGGGGSGGG GSDSSPLLQF GGQVRQRYLY TDDACQTEAH LEIREDGTVG GAADQSPESL LQLKALKPGV | Variant #204 = V101 with 15 AA Linker (GGGGS x 3) between Fc and FGF21 = (Q55C, A109T, G148C, K150R, P158S, S195A, P199G, G202A) |

TABLE 1-continued

FGF21 Variant Fc fusion proteins

| SEQ ID NO: | Sequence | Name* |
|---|---|---|
| | IQILGVKTSR FLCQRPDGTL YGSLHFDPEA CSFRELLLED GYNVYQSEAH GLPLHLPCNR SPHRDPASRG PARFLPLPGL PPALPEPPGI LAPQPPDVGS SDPLAMVGGS QARSPSYAS | |

*Note that the FGF21 wild-type sequence in this table refers to NCBI reference sequence number NP_061986.1 (SEQ ID NO: 1) unless otherwise specified. All mutations in the FGF21 moiety and corresponding amino acid numbering of said mutations refers back to (SEQ ID NO: 1) not to the full-length sequences in this table which may also include Fc and linker regions.

The variants or mutants used in the fusion proteins of the invention, e.g., variants of wild-type FGF21, feature at least one substituted, added, and/or removed amino acid relative to the wild-type protein. Additionally, the variants may include N- and/or C-terminal truncations relative to the wild-type proteins. Generally speaking, a variant possesses some modified property, structural or functional, of the wild-type protein. For example, the variant may have enhanced or improved physical stability in concentrated solutions (e.g., less hydrophobic mediated aggregation), enhanced or improved plasma stability when incubated with blood plasma or enhanced or improved bioactivity while maintaining a favorable bioactivity profile.

Acceptable amino acid substitutions and modifications which constitute differences between the portions of the fusion proteins of the invention and their wild-type comparator proteins include, but are not limited to, one or more amino acid substitutions, including substitutions with non-naturally occurring amino acid analogs, and truncations. Thus, the fusion proteins of the invention (e.g., the fusion proteins of the invention) include, but are not limited to, site-directed mutants, truncated polypeptides, proteolysis-resistant mutants, aggregation-reducing mutants, combination mutants, and fusion proteins, as described herein.

One skilled in the art of expression of proteins will recognize that methionine or methionine-arginine sequence can be introduced at the N-terminus of any of the fusion proteins of the invention, for expression in *E. coli*, and are contemplated within the context of this invention.

The fusion proteins of the invention may possess increased compatibility with pharmaceutical preservatives (e.g., m-cresol, phenol, benzyl alcohol), thus enabling the preparation of a preserved pharmaceutical formulation that maintains the physiochemical properties and biological activity of the protein during storage. Accordingly, variants with enhanced pharmaceutical stability relative to wild-type, have improved physical stability in concentrated solutions under both physiological and preserved pharmaceutical formulation conditions, while maintaining biological potency. By way of non-limiting example, the fusion proteins of the invention may be more resistant to proteolysis and enzymatic degradation; may have improved stability; and may be less likely to aggregate, than their wild-type counterparts or corresponding native sequence. As used herein, these terms are not mutually exclusive or limiting, it being entirely possible that a given variant has one or more modified properties of the wild-type protein.

The invention also encompasses nucleic acid molecules encoding the fusion proteins of the invention, comprising, for example, an FGF21 amino acid sequence that is at least about 95% identical to the amino acid sequence of SEQ ID NO:3, but wherein specific residues conferring a desirable property to the FGF21 protein variant, e.g., improved potency to FGF21-receptors, proteolysis-resistance, increased half life or aggregation-reducing properties and combinations thereof have not been further modified. In other words, with the exception of residues in the FGF21 mutant sequence that have been modified in order to confer proteolysis-resistance, aggregation-reducing, or other properties, about 5% (alternately 4%, alternately 3%, alternately 2%, alternately 1%) of all other amino acid residues in the FGF21 mutant sequence can be modified. Such FGF21 mutants possess at least one activity of the wild-type FGF21 polypeptide.

The invention also encompasses a nucleic acid molecule comprising a nucleotide sequence that is at least about 85%, identical, and more preferably, at least about 90 to 95% identical to the nucleotide sequence of SEQ ID NO:2 or SEQ ID NO:4, but wherein the nucleotides encoding amino acid residues conferring the encoded protein's proteolysis-resistance, aggregation-reducing or other properties have not been further modified. In other words, with the exception of nucleotides that encode residues in the FGF21 mutant sequences that have been modified in order to confer proteolysis-resistance, aggregation-reducing, or other properties, about 15%, and more preferably about 10 to 5% of all other nucleotides in the mutant sequence can be modified. Such nucleic acid molecules encode proteins possessing at least one activity of their wild-type counterparts.

Provided herein are methods used to generate the fusion proteins of the invention, wherein such methods involve site-specific modification and non-site-specific modification of the wild-type versions of the proteins (e.g., the FGF21 wild-type protein as described herein), e.g., truncations of the wild-type proteins, and the site-specific incorporation of amino acids at positions of interest within the wild-type proteins. Said modifications enhance the biological properties of the fusion proteins of the invention relative to the wild-type proteins, as well as, in some cases, serving as points of attachment for, e.g., labels and protein half-life extension agents, and for purposes of affixing said variants to the surface of a solid support. Related embodiments of the invention are methods of producing cells capable of producing said Fusion Proteins of the invention, and of producing vectors containing DNA encoding said variants.

In certain embodiments, such modifications, e.g., site-specific modifications, are used to attach conjugates, e.g., PEG groups to proteins, polypeptides, and/or peptides of the invention, for purposes of, e.g., extending half-life or otherwise improving the biological properties of said proteins, polypeptides, and/or peptides. Said techniques are described further herein.

In other embodiments, such modifications, e.g., site-specific modifications, are used to attach other polymers, small molecules and recombinant protein sequences that extend half-life of the protein of the invention. One such embodiment includes the attachment of fatty acids or specific albumin binding compounds to proteins, polypeptides, and/or peptides. In other embodiments, the modifications are made at a particular amino acid type and may be attached at one or more sites on the protein.

In other embodiments, such modifications, e.g., site-specific modifications, are used as means of attachment for the production of wild-type and/or variant multimers, e.g., dimers (homodimers or heterodimers) or trimers or tetramers. These multimeric protein molecules may additionally have groups such as PEG, sugars, and/or PEG-cholesterol conjugates attached or be fused either amino-terminally or carboxy-terminally to other proteins such as Fc, Human Serum Albumin (HSA), etc.

In other embodiments, such site-specific modifications are used to produce proteins, polypeptides and/or peptides wherein the position of the site-specifically incorporated pyrrolysine or pyrrolysine analogue or non-naturally occurring amino acids (para-acetyl-Phe, para-azido-Phe) allows for controlled orientation and attachment of such proteins, polypeptides and/or peptides onto a surface of a solid support or to have groups such as PEG, sugars and/or PEG-cholesterol conjugates attached.

In other embodiments, such site-specific modifications are used to site-specifically cross-link proteins, polypeptides and/or peptides thereby forming hetero-oligomers including, but not limited to, heterodimers and heterotrimers. In other embodiments, such site-specific modifications are used to site-specifically cross-link proteins, polypeptides and/or peptides thereby forming protein-protein conjugates, protein-polypeptide conjugates, protein-peptide conjugates, polypeptide-polypeptide conjugates, polypeptide-peptide conjugates or peptide-peptide conjugates. In other embodiments, a site specific modification may include a branching point to allow more than one type of molecule to be attached at a single site of a protein, polypeptide or peptide.

In other embodiments, the modifications listed herein can be done in a non-site-specific manner and result in protein-protein conjugates, protein-polypeptide conjugates, protein-peptide conjugates, polypeptide-polypeptide conjugates, polypeptide-peptide conjugates or peptide-peptide conjugates of the invention.

Definitions

Various definitions are used throughout this document. Most words have the meaning that would be attributed to those words by one skilled in the art. Words specifically defined either below or elsewhere in this document have the meaning provided in the context of the present invention as a whole and as are typically understood by those skilled in the art.

As used herein, the term "FGF21" refers to a member of the fibroblast growth factor (FGF) protein family. An amino acid sequence of FGF21 (GenBank Accession No. NP_061986.1) is set forth as SEQ ID NO:1, the corresponding polynucleotide sequence of which is set forth as SEQ ID NO:2 (NCBI reference sequence number NM_019113.2). "FGF21 variant," "FGF21 mutant," and similar terms describe modified version of the FGF21 protein, e.g., with constituent amino acid residues deleted, added, modified, or substituted.

As used herein, the term "FGF21 receptor" refers to a receptor for FGF21 (Kharitonenkov, A, et al. (2008) Journal of Cellular Physiology 215:1-7; Kurosu, H et al. (2007) JBC 282:26687-26695; Ogawa, Y et al. (2007) PNAS 104:7432-7437).

The term "FGF21 polypeptide" refers to a naturally-occurring polypeptide expressed in humans. For purposes of this disclosure, the term "FGF21 polypeptide" can be used interchangeably to refer to any full-length FGF21 polypeptide, e.g., SEQ ID NO:1, which consists of 209 amino acid residues and which is encoded by the nucleotide sequence of SEQ ID NO:2; any mature form of the polypeptide, which consists of 181 amino acid residues, and in which the 28 amino acid residues at the amino-terminal end of the full-length FGF21 polypeptide (i.e., which constitute the signal peptide) have been removed.

"Variant 76," as used herein, is an FGF21 protein variant, featuring a 40 kDa branched PEG linked through Cys154, and eight point mutations relative to the 177 amino acid wild-type protein. Synthesis of the variant is described in greater detail herein, and the protein sequence is represented in Table 1 and SEQ ID NO:9.

The term "isolated nucleic acid molecule" refers to a nucleic acid molecule of the present invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecules or other contaminants that are found in its natural environment that would interfere with its use in polypeptide production or its therapeutic, diagnostic, prophylactic or research use.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "operably linked" is used herein to refer to an arrangement of flanking sequences wherein the flanking sequences so described are configured or assembled so as to perform their usual function. Elements of fusions proteins may be operably linked to one another so as to allow the fusion protein to function as if it were a naturally occurring, endogenous protein, and/or to combine disparate elements of said fusion proteins in a synergistic fashion.

On a nucleotide level, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "amino acid," as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission.

The term "naturally occurring" when used in connection with biological materials such as nucleic acid molecules, polypeptides, host cells, and the like, refers to materials which are found in nature and are not manipulated by man. Similarly, "non-naturally occurring" as used herein refers to a material that is not found in nature or that has been structurally modified or synthesized by man. When used in connection with nucleotides, the term "naturally occurring" refers to the bases adenine (A), cytosine (C), guanine (G), thymine (T), and uracil (U). When used in connection with amino acids, the term "naturally occurring" refers to the 20 conventional amino acids (i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y)), as well as selenocysteine, pyrrolysine (Pyl, or O), and pyrroline-carboxy-lysine (Pcl, or Z).

Pyrrolysine (Pyl) is an amino acid naturally found within methylamine methyltransferases of methanogenic archaea of the family *Methanosarcina*. Pyrrolysine is a lysine analogue co-translationally incorporated at in-frame UAG codons in the respective mRNA, and it is considered the 22nd natural amino acid.

As described at least in PCT patent publication WO2010/48582 (applicant IRM, LLC), attempts to biosynthesize pyrrolysine (Pyl) in *E. coli* resulted in the formation of a "demethylated pyrrolysine," referred to herein as pyrroline-carboxy-lysine, or Pcl. "Pcl," as used herein, refers to either Pcl-A or Pcl-B.

The terms "non-natural amino acid" and "unnatural amino acid," as used herein, are interchangeably intended to represent amino acid structures that cannot be generated biosynthetically in any organism using unmodified or modified genes from any organism, whether the same or different. The terms refer to an amino acid residue that is not present in the naturally occurring (wild-type) FGF21 protein sequence or the sequences of the present invention. These include, but are not limited to, modified amino acids and/or amino acid analogues that are not one of the 20 naturally occurring amino acids, selenocysteine, pyrrolysine (Pyl), or pyrroline-carboxy-lysine (Pcl, e.g., as described in PCT patent publication WO2010/48582). Such non-natural amino acid residues can be introduced by substitution of naturally occurring amino acids, and/or by insertion of non-natural amino acids into the naturally occurring (wild-type) FGF21 protein sequence or the sequences of the invention. The non-natural amino acid residue also can be incorporated such that a desired functionality is imparted to the FGF21 molecule, for example, the ability to link a functional moiety (e.g., PEG).

When used in connection with amino acids, the symbol "U" shall mean "non-natural amino acid" and "unnatural amino acid," as used herein.

In addition, it is understood that such "unnatural amino acids" require a modified tRNA and a modified tRNA synthetase (RS) for incorporation into a protein. These "selected" orthogonal tRNA/RS pairs are generated by a selection process as developed by Schultz et al. or by random or targeted mutation. As way of example, pyrroline-carboxy-lysine is a "natural amino acid" as it is generated biosynthetically by genes transferred from one organism into the host cells and as it is incorporated into proteins by using natural tRNA and tRNA synthetase genes, while p-aminophenylalanine (See, Generation of a bacterium with a 21 amino acid genetic code, Mehl R A, Anderson J C, Santoro S W, Wang L, Martin A B, King D S, Horn D M, Schultz P G. J Am Chem Soc. 2003 January 29; 125(4): 935-9) is an "unnatural amino acid" because, although generated biosynthetically, it is incorporated into proteins by a "selected" orthogonal tRNA/tRNA synthetase pair.

Modified encoded amino acids include, but are not limited to, hydroxyproline, γ-carboxyglutamate, O-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. The term "amino acid" also includes naturally occurring amino acids that are metabolites in certain organisms but are not encoded by the genetic code for incorporation into proteins. Such amino acids include, but are not limited to, ornithine, D-ornithine, and D-arginine.

The term "amino acid analogue," as used herein, refers to compounds that have the same basic chemical structure as a naturally occurring amino acid, by way of example only, an α-carbon that is bound to a hydrogen, a carboxyl group, an amino group, and an R group. Amino acid analogues include the natural and unnatural amino acids which are chemically blocked, reversibly or irreversibly, or their C-terminal carboxy group, their N-terminal amino group and/or their side-chain functional groups are chemically modified. Such analogues include, but are not limited to, methionine sulfoxide, methionine sulfone, S-(carboxymethyl)-cysteine, S-(carboxymethyl)-cysteine sulfoxide, S-(carboxymethyl)-cysteine sulfone, aspartic acid-(beta-methyl ester), N-ethylglycine, alanine carboxamide, homoserine, norleucine, and methionine methyl sulfonium.

The term "amino acid mimetics," as used herein, refers to chemical compounds that have a structure that is different from the general chemical structure of an amino acid, but functions in a manner similar to a naturally occurring amino acid.

The term "biologically active variant" refers to any polypeptide variant used in the fusion proteins of the invention, e.g., as a constituent protein of the fusions, that possesses an activity of its wild-type (e.g., naturally-occurring) protein or polypeptide counterpart, such as the ability to modulate blood glucose, HbA1c, insulin, triglyceride, or cholesterol levels; increase pancreatic function; reduce lipid levels in liver; reduce body weight; and to improve glucose tolerance, energy expenditure, or insulin sensitivity, regardless of the type or number of modifications that have been introduced into the polypeptide variant. Polypeptide variants possessing a somewhat decreased level of activity relative to their wild-type versions can nonetheless be considered to be biologically active polypeptide variants. A non-limiting representative example of a biologically active polypeptide variant of the invention is an FGF21 variant, which is modified after, and possesses similar or enhanced biological properties relative to, wild-type FGF21.

The terms "effective amount" and "therapeutically effective amount" each refer to the amount of a fusion protein of the invention used to support an observable level of one or more biological activities of the wild-type polypeptide or protein counterparts, such as the ability to lower blood glucose, insulin, triglyceride or cholesterol levels; reduce liver triglyceride or lipid levels; reduce body weight; or improve glucose tolerance, energy expenditure, or insulin sensitivity. For example, a "therapeutically-effective amount" administered to a patient exhibiting, suffering, or prone to suffer from FGF21-associated disorders (such as type 1 or type 2 diabetes mellitus, obesity, or metabolic syndrome), is such an amount which induces, ameliorates or otherwise causes an improvement in the pathological symptoms, disease progression, physiological conditions associated with or resistance to succumbing to the aforementioned disorders. For the purposes of the present invention a "subject" or "patient" is preferably a human, but can also be an animal, more specifically, a companion animal (e.g., dogs, cats, and the like), farm animals (e.g., cows, sheep, pigs, horses, and the like) and laboratory animals (e.g., rats, mice, guinea pigs, and the like).

The term "pharmaceutically acceptable carrier" or "physiologically acceptable carrier" as used herein refers to one or more formulation materials suitable for accomplishing or enhancing the delivery of a fusion protein of the invention.

The term "antigen" refers to a molecule or a portion of a molecule that is capable of being bound by an antibody, and additionally that is capable of being used in an animal to produce antibodies that are capable of binding to an epitope of that antigen. An antigen may have one or more epitopes.

The term "native Fc" refers to molecule or sequence comprising the sequence of a non-antigen-binding fragment resulting from digestion of whole antibody or produced by other means, whether in monomeric or multimeric form, and can contain the hinge region. The original immunoglobulin source of the native Fc is preferably of human origin and can be any of the immunoglobulins, although IgG1 and IgG2 are preferred. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgA2). One example of a native Fc is a disulfide-bonded dimer resulting from papain digestion of an IgG (see Ellison et al., 1982, Nucleic Acids Res. 10: 4071-9). The term "native Fc" as used herein is generic to the monomeric, dimeric, and multimeric forms.

The term "Fc variant" refers to a molecule or sequence that is modified from a native Fc but still comprises a binding site for the salvage receptor, FcRn (neonatal Fc receptor). International Publication Nos. WO 97/34631 and WO 96/32478 describe exemplary Fc variants, as well as interaction with the salvage receptor, and are hereby incorporated by reference. Thus, the term "Fc variant" can comprise a molecule or sequence that is humanized from a non-human native Fc. Furthermore, a native Fc comprises regions that can be removed because they provide structural features or biological activity that are not required for the fusion molecules of the fusion proteins of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "Fc domain" encompasses native Fc and Fc variants and sequences as defined above. As with Fc variants and native Fc molecules, the term "Fc domain" includes molecules in monomeric or multimeric form, whether digested from whole antibody or produced by other means. In some embodiments of the present invention, an Fc domain can be fused to FGF21 or a FGF21 mutant (including a truncated form of FGF21 or a FGF21 mutant) via, for example, a covalent bond between the Fc domain and the FGF21 sequence. Such fusion proteins can form multimers via the association of the Fc domains and both these fusion proteins and their multimers are an aspect of the present invention.

The term "modified Fc fragment", as used herein, shall mean an Fc fragment of an antibody comprising a modified sequence. The Fc fragment is a portion of an antibody comprising the CH2, CH3 and part of the hinge region. The modified Fc fragment can be derived from, for example, IgGI, IgG2, IgG3, or IgG4. FcLALA is a modified Fc fragment with a LALA mutation (L234A, L235A), which triggers ADCC with lowered efficiency, and binds and activates human complement weakly. Hessell et al. 2007 Nature 449:101-104. Additional modifications to the Fc fragment are described in, for example, U.S. Pat. No. 7,217,798.

The term "heterologous" means that these domains are not naturally found associated with constant regions of an antibody. In particular, such heterologous binding domains do not have the typical structure of an antibody variable domain consisting of 4 framework regions, FR1, FR2, FR3 and FR4 and the 3 complementarity determining regions (CDRs) in-between. Each arm of the fusobody therefore comprises a first single chain polypeptides comprising a first binding domain covalently linked at the N-terminal part of a constant $C_H1$ heavy chain region of an antibody, and a second single chain polypeptide comprising a second binding domain covalently linked at the N-terminal part of a constant $C_L$ light chain of an antibody. The covalent linkage may be direct, for example via peptidic bound or indirect, via a linker, for example a peptidic linker. The two heterodimers of the fusobody are covalently linked, for example, by at least one disulfide bridge at their hinge region, like an antibody structure. Examples of molecules with a fusobody structure have been described in the art, in particular, fusobodies comprising ligand binding region of heterodimeric receptor (see for example international patent publications WO01/46261 and WO11/076781).

The term "polyethylene glycol" or "PEG" refers to a polyalkylene glycol compound or a derivative thereof, with or without coupling agents or derivatization with coupling or activating moieties.

The term "FGF21-associated disorders," and terms similarly used herein, includes obesity, type 1 and type 2 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, metabolic syndrome, acute myocardial infarction, hypertension, cardiovascular disease, atherosclerosis, peripheral arterial disease, stroke, heart failure, coronary heart disease, kidney disease, diabetic complications, neuropathy, gastroparesis, disorders associated with severe inactivating mutations in the insulin receptor, and other metabolic disorders.

The term "disorders associated with severe inactivating mutations in the insulin receptor," and terms similarly used herein, describe conditions in subjects afflicted with mutations in the insulin receptor (or possible proteins directly downstream from it) which cause severe insulin resistance but are often (though not always) seen without the obesity common in Type 2 diabetes mellitus. In many ways, subjects afflicted with these conditions manifest hybrid symptoms of Type 1 diabetes mellitus and Type 2 diabetes mellitus. Subjects thereby afflicted fall into several categories of roughly increasing severity, including: Type A Insulin Resistance, Type C Insulin Resistance (AKA HAIR-AN Syndrome), Rabson-Mendenhall Syndrome and finally Donohue's Syndrome or Leprechaunism. These disorders are associated with very high endogenous insulin levels, and very often, hyperglycemia. Subjects thereby afflicted also present with various clinical features associated with "insulin toxicity," including hyperandrogenism, polycystic ovarian syndrome (PCOS), hirsuitism, and acanthosis nigricans (excessive growth and pigmentation) in the folds of the skin.

"Type 2 diabetes mellitus" is a condition characterized by excess glucose production in spite of the availability of insulin, and circulating glucose levels remain excessively high as a result of inadequate glucose clearance.

"Type 1 diabetes mellitus" is a condition characterized by high blood glucose levels caused by total lack of insulin. This occurs when the body's immune system attacks the insulin-producing beta cells in the pancreas and destroys them. The pancreas then produces little or no insulin.

"Glucose intolerance" or Impaired Glucose Tolerance (IGT) is a pre-diabetic state of dysglycemia that is associated with increased risk of cardiovascular pathology. The pre-diabetic condition prevents a subject from moving glucose into cells efficiently and utilizing it as an efficient fuel source, leading to elevated glucose levels in blood and some degree of insulin resistance.

"Hyperglycemia" is defined as an excess of sugar (glucose) in the blood.

"Hypoglycemia", also called low blood sugar, occurs when your blood glucose level drops too low to provide enough energy for your body's activities.

"Hyperinsulinemia" is defined as a higher-than-normal level of insulin in the blood.

"Insulin resistance" is defined as a state in which a normal amount of insulin produces a subnormal biologic response.

"Obesity," in terms of the human subject, can be defined as that body weight over 20 percent above the ideal body weight for a given population (R. H. Williams, Textbook of Endocrinology, 1974, p. 904-916).

"Diabetic complications" are problems, caused by high blood glucose levels, with other body functions such as kidneys, nerves (neuropathies), feet (foot ulcers and poor circulation) and eyes (e.g. retinopathies). Diabetes also increases the risk for heart disease and bone and joint disorders. Other long-term complications of diabetes include skin problems, digestive problems, sexual dysfunction and problems with teeth and gums.

"Metabolic syndrome" can be defined as a cluster of at least three of the following signs: abdominal fat—in most men, a 40-inch waist or greater; high blood sugar—at least 110 milligrams per deciliter (mg/dl) after fasting; high triglycerides—at least 150 mg/dL in the bloodstream; low HDL—less than 40 mg/dl; and, blood pressure of 130/85 mmHg or higher.

"Pancreatitis" is inflammation of the pancreas.

"Dyslipidemia" is a disorder of lipoprotein metabolism, including lipoprotein overproduction or deficiency. Dyslipidemias may be manifested by elevation of the total cholesterol, low-density lipoprotein (LDL) cholesterol and triglyceride concentrations, and a decrease in high-density lipoprotein (HDL) cholesterol concentration in the blood.

"Nonalcoholic fatty liver disease (NAFLD)" is a liver disease, not associated with alcohol consumption, characterized by fatty change of hepatocytes.

"Nonalcoholic steatohepatitis (NASH)" is a liver disease, not associated with alcohol consumption, characterized by fatty change of hepatocytes, accompanied by intralobular inflammation and fibrosis.

"Hypertension" or high blood pressure that is a transitory or sustained elevation of systemic arterial blood pressure to a level likely to induce cardiovascular damage or other adverse consequences. Hypertension has been arbitrarily defined as a systolic blood pressure above 140 mmHg or a diastolic blood pressure above 90 mmHg.

"Cardiovascular diseases" are diseases related to the heart or blood vessels.

"Acute myocardial infarction" occurs when there is interruption of the blood supply to a part of the heart. The resulting ischemia and oxygen shortage, if left untreated for a sufficient period of time, can cause damage or death (infarction) of the heart muscle tissue (myocardium).

"Peripheral arterial disease" occurs when plaque builds up in the arteries that carry blood to the head, organs and limbs. Over time, plaque can harden and narrow the arteries which limits the flow of oxygen-rich blood to organs and other parts of the body.

"Atherosclerosis" is a vascular disease characterized by irregularly distributed lipid deposits in the intima of large and medium-sized arteries, causing narrowing of arterial lumens and proceeding eventually to fibrosis and calcification. Lesions are usually focal and progress slowly and intermittently. Limitation of blood flow accounts for most clinical manifestations, which vary with the distribution and severity of lesions.

"Stroke" is any acute clinical event, related to impairment of cerebral circulation, that lasts longer than 24 hours. A stroke involves irreversible brain damage, the type and severity of symptoms depending on the location and extent of brain tissue whose circulation has been compromised.

"Heart failure", also called congestive heart failure, is a condition in which the heart can no longer pump enough blood to the rest of the body.

"Coronary heart disease", also called coronary artery disease, is a narrowing of the small blood vessels that supply blood and oxygen to the heart.

"Kidney disease" or nephropathy is any disease of the kidney. Diabetic nephropathy is a major cause of morbidity and mortality in people with type 1 or type 2 diabetes mellitus.

"Neuropathies" are any diseases involving the cranial nerves or the peripheral or autonomic nervous system.

"Gastroparesis" is weakness of gastric peristalsis, which results in delayed emptying of the bowels.

The critically ill patients encompassed by the present invention generally experience an unstable hypermetabolic state. This unstable metabolic state is due to changes in substrate metabolism, which may lead to relative deficiencies in some nutrients. Generally there is an increased oxidation of both fat and muscle.

Moreover, critically ill patients are preferably patients that experience systemic inflammatory response syndrome or respiratory distress. A reduction in morbidity means reducing the likelihood that a critically ill patient will develop additional illnesses, conditions, or symptoms or reducing the severity of additional illnesses, conditions, or symptoms. For example reducing morbidity may correspond to a decrease in the incidence of bacteremia or sepsis or complications associated with multiple organ failure.

As used herein, the singular forms "a," "an" and "the" include plural references unless the content clearly dictates otherwise. Thus, for example, reference to "an antibody" includes a mixture of two or more such antibodies.

As used herein, the term "about" refers to +/−20%, more preferably, +/−10%, or still more preferably, +/−5% of a value.

The terms "polypeptide" and "protein", are used interchangeably and refer to a polymeric form of amino acids of any length, which can include coded and non-coded amino acids, naturally and non-naturally occurring amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "individual", "subject", "host" and "patient" are used interchangeably and refer to any subject for whom diagnosis, treatment, or therapy is desired, particularly humans. Other subjects may include cattle, dogs, cats, guinea pigs, rabbits, rats, mice, horses, and the like. In some preferred embodiments the subject is a human.

As used herein, the term "sample" refers to biological material from a patient. The sample assayed by the present invention is not limited to any particular type. Samples include, as non-limiting examples, single cells, multiple cells, tissues, tumors, biological fluids, biological molecules, or supernatants or extracts of any of the foregoing. Examples include tissue removed for biopsy, tissue removed during resection, blood, urine, lymph tissue, lymph fluid, cerebrospinal fluid, mucous, and stool samples. The sample used will vary based on the assay format, the detection method and the nature of the tumors, tissues, cells or extracts to be assayed. Methods for preparing samples are well known in the art and can be readily adapted in order to obtain a sample that is compatible with the method utilized.

As used herein, the term "biological molecule" includes, but is not limited to, polypeptides, nucleic acids, and saccharides.

As used herein, the term "modulating" refers to a change in the quality or quantity of a gene, protein, or any molecule that is inside, outside, or on the surface of a cell. The change can be an increase or decrease in expression or level of the molecule. The term "modulates" also includes changing the quality or quantity of a biological function/activity including, without limitation, the ability to lower blood glucose, insulin, triglyceride, or cholesterol levels; to reduce liver lipid or liver triglyceride levels; to reduce body weight; and to improve glucose tolerance, energy expenditure, or insulin sensitivity.

As used herein, the term "modulator" refers to a composition that modulates one or more physiological or biochemical events associated with an FGF21-associated disorder, such as type 1 or type 2 diabetes mellitus or a metabolic condition like obesity. Said events include but are not limited to the ability to lower blood glucose, insulin, triglyceride, or cholesterol levels; to reduce liver lipid or liver triglyceride levels; to reduce body weight; and to improve glucose tolerance, energy expenditure, or insulin sensitivity.

A "gene product" is a biopolymeric product that is expressed or produced by a gene. A gene product may be, for example, an unspliced RNA, an mRNA, a splice variant mRNA, a polypeptide, a post-translationally modified polypeptide, a splice variant polypeptide etc. Also encompassed by this term are biopolymeric products that are made using an RNA gene product as a template (i.e. cDNA of the RNA). A gene product may be made enzymatically, recombinantly, chemically, or within a cell to which the gene is native. In some embodiments, if the gene product is proteinaceous, it exhibits a biological activity. In some embodiments, if the gene product is a nucleic acid, it can be translated into a proteinaceous gene product that exhibits a biological activity.

"Modulation of FGF21 activity," as used herein, refers to an increase or decrease in FGF21 activity that can be a result of, for example, interaction of an agent with an FGF21 polynucleotide or polypeptide, inhibition of FGF21 transcription and/or translation (e.g., through antisense or siRNA interaction with the FGF21 gene or FGF21 transcript, through modulation of transcription factors that facilitate FGF21 expression), and the like. For example, modulation of a biological activity refers to an increase or a decrease in a biological activity. FGF21 activity can be assessed by means including, without limitation, assaying blood glucose, insulin, triglyceride, or cholesterol levels in a subject, assessing FGF21 polypeptide levels, or by assessing FGF21 transcription levels. Comparisons of FGF21 activity can also be accomplished by, e.g., measuring levels of an FGF21 downstream biomarker, and measuring increases in FGF21 signaling. FGF21 activity can also be assessed by measuring: cell signaling; kinase activity; glucose uptake into adipocytes; blood insulin, triglyceride, or cholesterol level fluctuations; liver lipid or liver triglyceride level changes; interactions between FGF21 and an FGF21 receptor; or phosphorylation of an FGF21 receptor. In some embodiments phosphorylation of an FGF21 receptor can be tyrosine phosphorylation. In some embodiments modulation of FGF21 activity can cause modulation of an FGF21-related phenotype.

Comparisons of FGF21 activity can also be accomplished by, e.g., measuring levels of an FGF21 downstream biomarker, and measuring increases in FGF21 signaling. FGF21 activity can also be assessed by measuring: cell signaling; kinase activity; glucose uptake into adipocytes; blood insulin, triglyceride, or cholesterol level fluctuations; liver lipid or liver triglyceride level changes; interactions between FGF21 and a receptor (FGFR-1c, FGFR-2c, or FGFR-3c); or phosphorylation of an FGF21 receptor. In some embodiments phosphorylation of an FGF21 receptor can be tyrosine phosphorylation. In some embodiments modulation of FGF21 activity can cause modulation of an FGF21-related phenotype.

A "FGF21 downstream biomarker," as used herein, is a gene or gene product, or measurable indicia of a gene or gene product. In some embodiments, a gene or activity that is a downstream marker of FGF21 exhibits an altered level of expression, or in a vascular tissue. In some embodiments, an activity of the downstream marker is altered in the presence of an FGF21 modulator. In some embodiments, the downstream markers exhibit altered levels of expression when FGF21 is perturbed with an FGF21 modulator of the present invention. FGF21 downstream markers include, without limitation, glucose or 2-deoxy-glucose uptake, pERK and other phosphorylated or acetylated proteins or NAD levels.

As used herein, the term "up-regulates" refers to an increase, activation or stimulation of an activity or quantity. For example, in the context of the present invention, FGF21 modulators may increase the activity of an FGF21 receptor. In one embodiment, one or more FGFR-1c, FGFR-2c, or FGFR-3c may be upregulated in response to an FGF21 modulator. Upregulation can also refer to an FGF21-related activity, such as e.g., the ability to lower blood glucose, insulin, triglyceride, or cholesterol levels; to reduce liver lipid or triglyceride levels; to reduce body weight; to improve glucose tolerance, energy expenditure, or insulin sensitivity; or to cause phosphorylation of an FGF21 receptor; or to increase an FGF21 downstream marker. The FGFR21 receptor can be one or more of FGFR-1c, FGFR-2c, or FGFR-3c. Up-regulation may be at least 25%, at least 50%, at least 75%, at least 100%, at least 150%, at least 200%, at least 250%, at least 400%, or at least 500% as compared to a control.

As used herein, the term "N-terminus" refers to at least the first 20 amino acids of a protein.

As used herein, the terms "N-terminal domain" and "N-terminal region" are used interchangeably and refer to a fragment of a protein that begins at the first amino acid of the protein and ends at any amino acid in the N-terminal half of the protein. For example, the N-terminal domain of FGF21 is from amino acid 1 of SEQ ID NO:1 to any amino acid between about amino acids 10 and 105 of SEQ ID NO:1.

As used herein, the term "C-terminus" refers to at least the last 20 amino acids of a protein.

As used herein, the terms "C-terminal domain" and "C-terminal region" are used interchangeably and refer to a fragment of a protein that begins at any amino acid in the C-terminal half of the protein and ends at the last amino acid of the protein. For example, the C-terminal domain of FGF21 begins at any amino acid from amino acid 105 to about amino acid 200 of SEQ ID NO:1 and ends at amino acid 209 of SEQ ID NO:1.

The term "domain" as used herein refers to a structural part of a biomolecule that contributes to a known or suspected function of the biomolecule. Domains may be coextensive with regions or portions thereof and may also incorporate a portion of a biomolecule that is distinct from a particular region, in addition to all or part of that region.

As used herein, the term "signal domain" (also called "signal sequence" or "signal peptide") refers to a peptide domain that resides in a continuous stretch of amino acid sequence at the N-terminal region of a precursor protein (often a membrane-bound or secreted protein) and is involved in post-translational protein transport. In many cases the signal domain is removed from the full-length protein by specialized signal peptidases after the sorting process has been completed. Each signal domain specifies a particular destination in the cell for the precursor protein. The signal domain of FGF21 is amino acids 1-28 of SEQ ID NO:1.

As used herein, the term "receptor binding domain" refers to any portion or region of a protein that contacts a membrane-bound receptor protein, resulting in a cellular response, such as a signaling event.

As used herein, the term "ligand binding domain" refers to any portion or region of a fusion protein of the invention retaining at least one qualitative binding activity of a corresponding native sequence.

The term "region" refers to a physically contiguous portion of the primary structure of a biomolecule. In the case of proteins, a region is defined by a contiguous portion of the amino acid sequence of that protein. In some embodiments a "region" is associated with a function of the biomolecule.

The term "fragment" as used herein refers to a physically contiguous portion of the primary structure of a biomolecule. In the case of proteins, a portion is defined by a contiguous portion of the amino acid sequence of that protein and refers to at least 3-5 amino acids, at least 8-10 amino acids, at least 11-15 amino acids, at least 17-24 amino acids, at least 25-30 amino acids, and at least 30-45 amino acids. In the case of oligonucleotides, a portion is defined by a contiguous portion of the nucleic acid sequence of that oligonucleotide and refers to at least 9-15 nucleotides, at least 18-30 nucleotides, at least 33-45 nucleotides, at least 48-72 nucleotides, at least 75-90 nucleotides, and at least 90-130 nucleotides. In some embodiments, portions of biomolecules have a biological activity. In the context of the present invention, FGF21 polypeptide fragments do not comprise the entire FGF21 polypeptide sequence set forth in SEQ ID NO:1.

A "native sequence" polypeptide is one that has the same amino acid sequence as a polypeptide derived from nature. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

As used herein, the phrase "homologous nucleotide sequence," or "homologous amino acid sequence," or variations thereof, refers to sequences characterized by a homology, at the nucleotide level or amino acid level, of at least a specified percentage and is used interchangeably with "sequence identity." Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than humans, including, but not limited to, mammals. Homologous nucleotide sequences also include, but are not limited to, naturally occurring allelic variations and mutations of the nucleotide sequences set forth herein. Homologous amino acid sequences include those amino acid sequences which contain conservative amino acid substitutions and which polypeptides have the same binding and/or activity. In some embodiments, a nucleotide or amino acid sequence is homologous if it has at least 60% or greater, up to 99%, identity with a comparator sequence. In some embodiments, a nucleotide or amino acid sequence is homologous if it shares one or more, up to 60, nucleotide/amino acid substitutions, additions, or deletions with a comparator sequence. In some embodiments, the homologous amino acid sequences have no more than 5 or no more than 3 conservative amino acid substitutions.

Percent homology or identity can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489). In some embodiments, homology between the probe and target is between about 75% to about 85%. In some embodiments, nucleic acids have nucleotides that are at least about 95%, about 97%, about 98%, about 99% and about 100% homologous to SEQ ID NO:2, or a portion thereof.

Homology may also be at the polypeptide level. In some embodiments, constituent polypeptides of the fusion proteins of the invention may be at least 95% homologous to their full length wild-type counterparts or corresponding native sequences, or to portions thereof. The degree or percentage identity of Fusion Proteins of the invention, or portions thereof, and different amino acid sequences is calculated as the number of exact matches in an alignment of the two sequences divided by the length of the "invention sequence" or the "foreign sequence", whichever is shortest. The result is expressed as percent identity.

As used herein, the term "mixing" refers to the process of combining one or more compounds, cells, molecules, and the like together in the same area. This may be performed, for example, in a test tube, petri dish, or any container that allows the one or more compounds, cells, or molecules, to be mixed.

As used herein, the term "substantially purified" refers to a compound (e.g., either a polynucleotide or a polypeptide or an antibody) that is removed from its natural environment and is at least 60% free, at least 75% free, and at least 90% free from other components with which it is naturally associated.

The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, lipid aggregates and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles.

Enhancing the Physical Stability of the Fusion Proteins of the Invention

Naturally occurring disulfide bonds, as provided by cysteine residues, generally increase thermodynamic stability of proteins. Successful examples of increased thermodynamic stability, as measured in increase of the melting temperature, are multiple disulfide-bonded mutants of the enzymes T4 lysozyme (Matsumura et al., PNAS 86:6562-6566 (1989)) and barnase (Johnson et al., J. Mol. Biol. 268:198-208 (1997)). An aspect of the present invention is an enhancement of the physical stability of FGF21 in the presence of a preservative, achieved by the presence of disulfide bonds within the variants, which constrain the flexibility of wild-type FGF21 and thereby limit access of the preservative to the hydrophobic core of the protein.

The second aspect of the present invention therefore provides variants of human FGF21, or a biologically active peptide thereof, with enhanced pharmaceutical stability engendered by the incorporation of additional disulfide bonds, e.g., via incorporating or substituting cysteine residues into the wild-type FGF21 protein or the polypeptide and protein variants of the invention. One skilled in the art will recognize that the native cysteines, cysteine 103 and cysteine 121, could be utilized as loci to introduce a novel disulfide bond that may impart improved properties, in addition to the suggested embodiments described herein.

These include fusion proteins which incorporate wild-type FGF-21 with the substitution of a cysteine for two or more of the following: glutamine 46, arginine 47, tyrosine 48, leucine 49, tyrosine 50, threonine 51, aspartate 52, aspartate 53, alanine 54, glutamine 55, glutamine 56, threonine 57, glutamate 58, alanine 59, histidine 60, leucine 61, glutamate 62, isoleucine 63, valine 69, glycine 70, glycine 71, alanine 72, alanine 73, leucine 144, histidine 145, leucine 146, proline 147, glycine 148, asparagine 149, lysine 150, serine 151, proline 152, histidine 153, arginine 154, aspartate 155, proline 156, alanine 157, proline 158, arginine 159, glycine 160, proline 161, alanine 162, arginine 163. phenylalanine 164, wherein the numbering of the amino acids is based on the full length 209 amino acid hFGF21 sequence SEQ ID NO:1

Furthermore, fusion proteins of the invention may incorporate variants of wild-type human FGF21, or a biologically active peptide thereof, which are enhanced with engineered disulfide bonds, in addition to the naturally occurring one at Cys103-Cys121, are as follows: Gln46Cys-Ala59Cys, Gln46Cys-His60Cys, Gln46Cys-Leu61Cys, Gln46Cys-Glu62Cys, Gln46Cys-Ile63Cys, Arg47Cys-Ala59Cys, Arg47Cys-His60Cys, Arg47Cys-Leu61Cys, Arg47Cys-Glu62Cys, Arg47Cys-Ile63Cys, Tyr48Cys-Ala59Cys, Tyr48Cys-His60Cys, Tyr48Cys-Leu61Cys, Tyr48Cys-Glu62Cys, Tyr48Cys-Ile63Cys, Leu49Cys-Ala59Cys, Leu49Cys-His60Cys, Leu49Cys-Leu61Cys, Leu49Cys-Glu62Cys, Leu49Cys-Ile63Cys, Tyr50Cys-Ala59Cys, Tyr50Cys-His60Cys, Tyr50Cys-Lue61Cys, Tyr50Cys-Glu62Cys, Tyr50Cys-Ile63Cys, Leu144Cys-Gly160Cys, Leu144Cys-Pro161Cys, Leu144Cys-Ala162Cys, Leu144Cys-Arg163Cys, Leu144Cys-Phe164Cys, His145Cys-Gly160Cys, His145Cys-Pro161Cys, His145Cys-Ala162Cys, His145Cys-Arg163Cys, His145Cys-Phe164Cys, Leu146Cys-Gly160Cys, Leu146Cys-Pro161Cys, Leu146Cys-Ala162Cys, Leu146Cys-Arg163Cys, Leu146Cys-Phe164Cys, Pro147Cys-Gly160Cys, Pro147Cys-Pro161Cys, Pro147Cys-Ala162Cys, Pro147Cys-Arg163Cys, Pro147Cys-Phe164Cys, Gly148Cys-Gly160Cys, Gly148Cys-Pro161Cys, Gly148Cys-Ala162Cys, Gly148Cys-Arg163Cys, Gly148Cys-Phe164Cys, Thr57Cys-Val69Cys, Thr57Cys-Gly70Cys, Thr57Cys-Gly71Cys, Thr57Cys-Ala72Cys, Thr57Cys-Ala73Cys, Glu58Cys-Val69Cys, Glu58Cys-Glu70Cys, Glu58Cys-G71Cys, Glu58Cys-Ala72Cys, Glu58Cys-Ala73Cys, Ala59Cys-Val69Cys, Ala59Cys-Gly70Cys, Ala59Cys-Gly71Cys, Ala59Cys-Ala72Cys, Ala59Cys-Ala73Cys, His60Cys-Val69Cys, His60Cys-Gly70Cys, His60Cys-Gly71Cys, His60Cys-Ala72Cys, His60Cys-Ala73Cys, Leu61Cys-Val69Cys, Leu61Cys-Gly70Cys, Leu61Cys-Gly71Cys, Leu61Cys-Ala72Cys, Leu61Cys-Ala73Cys, Arg47Cys-Gly148Cys, Tyr48Cys-Gly148Cys, Leu49Cys-Gly148Cys, Tyr50Cys-Gly148Cys, Thr51Cys-Gly148Cys, Asp52Cys-Gly148Cys, Asp53Cys-Gly148Cys, Ala54Cys-Gly148Cys, Gln55Cys-Gly148Cys, Gln56Cys-Gly148Cys, Thr57Cys-Gly148Cys, Glu58Cys-Gly148Cys, Arg47Cys-Asn149Cys, Tyr48Cys-Asn149Cys, Leu49Cys-Asn149Cys, Tyr50Cys-Asn149Cys, Thr51Cys-Asn149Cys, Asp52Cys-Asn149Cys, Asp53Cys-Asn149Cys, Ala54Cys-Asn149Cys, Gln55Cys-Asn149Cys, Gln56Cys-Asn149Cys, Thr57Cys-Asn149Cys, Glu58Cys-Asn149Cys, Arg47Cys-Lys150Cys, Tyr48Cys-Lys150Cys, Leu49Cys-Lys150Cys, Tyr50Cys-Lys150Cys, Thr51Cys-Lys150Cys, Asp52Cys-Lys150Cys, Asp53Cys-Lys150Cys, Ala54Cys-Lys150Cys, Gln55Cys-Lys150Cys, Gln56Cys-Lys150Cys, Thr57Cys-Lys150Cys, Glu58Cys-Lys150Cys, Arg47Cys-Ser151Cys, Tyr48Cys-Ser151Cys, Leu49Cys-Ser151Cys, Tyr50Cys-Ser151Cys, Thr51Cys-Ser151Cys, Asp52Cys-Ser151Cys, Asp53Cys-Ser151Cys, Ala54Cys-Ser151Cys, Gln55Cys-Ser151Cys, Gln56Cys-Ser151Cys, Thr57Cys-Ser151Cys, Glu58Cys-Ser151Cys, Arg47Cys-Pro152Cys, Tyr48Cys-Pro152Cys, Leu49Cys-Pro152Cys, Tyr50Cys-Pro152Cys, Thr51Cys-Pro152Cys, Asp52Cys-Pro152Cys, Asp53Cys-Pro152Cys, Ala54Cys-Pro152Cys, Gln55Cys-Pro152Cys, Gln56Cys-Pro152Cys, Thr57Cys-Pro152Cys, Glu58Cys-Pro152Cys, Arg47Cys-His153Cys, Tyr48Cys-His153Cys, Leu49Cys-His153Cys, Tyr50Cys-His153Cys, Thr51Cys-His153Cys, Asp52Cys-His153Cys, Asp53Cys-His153Cys, Ala54Cys-His153Cys, Gln55Cys-His153Cys, Gln56Cys-His153Cys, Thr57Cys-His153Cys, Glu58Cys-His153Cys, Arg47Cys-Arg154Cys, Tyr48Cys-Arg154Cys, Leu49Cys-Arg154Cys, Tyr50Cys-Arg154Cys, Thr51Cys-Arg154Cys, Asp52Cys-Arg154Cys, Asp53Cys-Arg154Cys, Ala54Cys-Arg154Cys, Gln55Cys-Arg154Cys, Gln56Cys-Arg154Cys, Thr57Cys-Arg154Cys, Glu58Cys-Arg154Cys, Arg47Cys-Asp155Cys, Tyr48Cys-Asp155Cys, Leu49Cys-Asp155Cys, Tyr50Cys-Asp155Cys, Thr51Cys-Asp155Cys, Asp52Cys-Asp155Cys, Asp53Cys-Asp155Cys, Ala54Cys-Asp155Cys, Gln55Cys-Asp155Cys, Gln56Cys-Asp155Cys, Thr57Cys-Asp155Cys, Glu58Cys-Asp155Cys, Arg47Cys-Pro156Cys, Tyr48Cys-Pro156Cys, Leu49Cys-Pro156Cys, Tyr50Cys-Pro156Cys, Thr51Cys-Pro156Cys, Asp52Cys-Pro156Cys, Asp53Cys-Pro156Cys, Ala54Cys-Pro156Cys, Gln55Cys-Pro156Cys, Gln56Cys-Pro156Cys, Thr57Cys-Pro156Cys, Glu58Cys-Pro156Cys, Arg47Cys-Ala157Cys, Tyr48Cys-Ala157Cys, Leu49Cys-Ala157Cys, Tyr50Cys-Ala157Cys, Thr51Cys-Ala157Cys, Asp52Cys-Ala157Cys, Asp53Cys-Ala157Cys, Ala54Cys-Ala157Cys, Gln55Cys-Ala157Cys, Gln56Cys-Ala157Cys, Thr57Cys-Ala157Cys, Glu58Cys-Ala157Cys, Arg47Cys-Pro158Cys, Tyr48Cys-Pro158Cys, Leu49Cys-Pro158Cys, Tyr50Cys-Pro158Cys, Thr51Cys-Pro158Cys, Asp52Cys-Pro158Cys, Asp53Cys-Pro158Cys, Ala54Cys-Pro158Cys, Gln55Cys-Pro158Cys, Gln56Cys-Pro158Cys, Thr57Cys-Pro158Cys, Glu58Cys-Pro158Cys, Arg47Cys-Arg159Cys, Tyr48Cys-Arg159Cys, Leu49Cys-Arg159Cys, Tyr50Cys-Arg159Cys, Thr51Cys-Arg159Cys, Asp52Cys-Arg159Cys, Asp53Cys-Arg159Cys, Ala54Cys-Arg159Cys, Gln55Cys-Arg159Cys, Gln56Cys-Arg159Cys, Thr57Cys-Arg159Cys, Glu58Cys-Arg159Cys, Arg47Cys-G160Cys, Tyr48Cys-G160Cys, Leu49Cys-G160Cys, Tyr50Cys-Gly160Cys, Thr51Cys-Gly160Cys, Asp52Cys-Gly160Cys, Asp53Cys-Gly160Cys, Ala54Cys-Gly160Cys, Gln55Cys-Gly160Cys, Gln56Cys-Gly160Cys, Thr57Cys-Gly160Cys, Glu58Cys-Gly160Cys, Arg47Cys-Pro161Cys, Tyr48Cys-Pro161Cys, Leu49Cys-Pro161Cys, Tyr50Cys-Pro161Cys, Thr51Cys-Pro161Cys, Asp52Cys-Pro161Cys, Asp53Cys-Pro161Cys, Ala54Cys-Pro161Cys, Gln55Cys-Pro161Cys, Gln56Cys-Pro161Cys, Thr57Cys-Pro161Cys, Glu58Cys-Pro161Cys, Arg47Cys-Ala162Cys, Tyr48Cys-Ala162Cys, Leu49Cys-Ala162Cys, Tyr50Cys-Ala162Cys, Thr51Cys-Ala162Cys, Asp52Cys-Ala162Cys, Asp53Cys-Ala162Cys, Ala54Cys-Ala162Cys, Gln55Cys-Ala162Cys, Gln56Cys-Ala162Cys, Thr57Cys-Ala162Cys, Glu58Cys-Ala162Cys, Arg47Cys-Arg163Cys, Tyr48Cys-Arg163Cys, Leu49Cys-Arg163Cys, Tyr50Cys-Arg163Cys, Thr51Cys-Arg163Cys, Asp52Cys-Arg163Cys, Asp53Cys-Arg163Cys, Ala54Cys-Arg163Cys, Gln55Cys-Arg163Cys, Gln56Cys-Arg163Cys, Thr57Cys-Arg163Cys, Glu58Cys-Arg163Cys Another aspect of the present invention provides fusion proteins comprising variants of wild-type human FGF21, or a biologically active peptide thereof, comprising a substitution of any charged and/or polar but uncharged amino acid at any of the amino acid positions indicated in the first embodiment of the present invention combined with the substitution of a cysteine at two or more amino acid positions indicated in the second embodiment of the invention.

Improvements of the Fusion Proteins of the Invention Over Wild Type Protein Comparators and Variants Thereof It is well known in the art that a significant challenge in the development of protein pharmaceuticals is to deal with the physical and chemical instabilities of proteins. This is even more apparent when a protein pharmaceutical formulation is intended to be a multiple use, injectable formulation requiring a stable, concentrated and preserved solution, while maintaining a favorable bioactivity profile. Biophysical characterization of wild-type FGF21 in the literature established that a concentrated protein solution (>5 mg/ml), when exposed to stress conditions, such as high temperature or low pH, lead to accelerated association and aggregation (i.e., poor physical stability and biopharmaceutical properties). Exposure of a concentrated protein solution of FGF21 to pharmaceutical preservatives (e.g., m-cresol) also had a negative impact on physical stability.

Therefore, an embodiment of the present invention is to enhance physical stability of concentrated solutions, while maintaining chemical stability and biological potency, under both physiological and preserved formulation conditions. It is thought that association and aggregation may result from hydrophobic interactions, since, at a given protein concentration, temperature, and ionic strength have considerable impact on physical stability. For the most part, non-conserved, presumed surface exposed amino acid residues were targeted. The local environment of these residues was analyzed and, those that were not deemed structurally important were selected for mutagenesis. One method to initiate specific changes is to further decrease the pI of the protein by introducing glutamic acid residues ("glutamic acid scan"). It is hypothesized that the introduction of charged substitutes would inhibit hydrophobic-mediated aggregation via charge-charge repulsion and potentially improve preservative compatibility. In addition, one skilled in the art would also recognize that with sufficient degree of mutagenesis the pI could be shifted into a basic pH range by the introduction of positive charge with or without concomitant decrease in negative charge, thus allowing for charge-charge repulsion.

An additional difficulty associated with therapeutic applications of wild-type FGF21 as a biotherapeutic, for instance, is that its half-life is very short in vivo (on the order of 0.5 and 2 h, respectively, in mouse and primate). There is hence a need to develop follow-up compounds that are more efficacious either through higher potency or longer half-life. The fusion proteins of the invention were developed as a way to achieve the desirable effects of FGF21 treatment at a higher potency and in a half-life-extended formulation.

As described further herein, the fusion proteins of the invention have half-lives of greater than two weeks in the mouse, compared to the much shorter half-life of wild-type FGF21 and the 17 hour half-life of fusion protein Fc-L (15)-FGF21 (L98R, P171G, A180E) in PCT Publication WO10/129600. The fusion proteins of the invention also demonstrate improved half-life and pharmacokinetic properties compared to PEGylated V76, as described herein and in U.S. patent application 61/415,476, filed on Nov. 19, 2010.

Furthermore, the Fc-FGF21 fusion proteins of the invention at 1 mpk are more efficacious than V76 at 5 mpk on reducing glucose, insulin, body weight and liver lipid. In a 12-day treatment study in ob/ob mice, the fusion proteins show the following % changes from vehicle (all of the fusions are administered at 1.0 mg/kg, and V76 is administered at 5.0 mg/kg):

Total glucose (AUC) % change from vehicle: V76 is −42%; V101 is −53%, V103 is −46%, and V188 is −42%;

Total plasma insulin % change from vehicle: V76 is −46%; V101 is −82%, V103 is −69%, and V188 is −59%;

Total body weight % change from vehicle: V76 is −7%; V101 is −12%, V103 is −12%, and V188 is −11%; and Total liver lipid % change from vehicle: V76 is −30%; V101 is −44%, V103 is −50%, and V188 is −51%.

Similarly, in vitro assays reveal the same 5-fold or greater potency of the fusion proteins of the invention over V76:

In the pERK in human adipocytes assay (mean EC50±SEM), V76 is 21±2 nM (n=3); V101 is 1.0±0.1 nM (n=3), V103 is 1.3±0.2 nM (n=3), and V188 is 1.4±0.4 nM (n=3);

In the pERK in HEK293 with human βklotho assay (mean EC50±SEM), V76 is 13±4 nM (n=5), V101 is 0.60±0.06 nM (n=5), V103 is 0.9±0.3 nM (n=5), and V188 is 0.4±0.1 nM (n=3); and In the glucose uptake in mouse adipocytes assay (mean EC50±SEM), V76 is 5±1 nM (n=3), V101 is 0.60±0.06 nM (n=3), V103 is 0.60±0.07 nM (n=3), and V188 is 0.48±0.14 nM (n=3).

Although the embodiments of the present invention concern the physical and chemical stability under both physiological and preserved pharmaceutical formulation conditions, maintaining the biological potency of the fusion proteins of the invention as compared to, e.g., wild-type FGF21 is an important factor of consideration as well. Therefore, the biological potency of the proteins of the present invention is defined by the ability of the proteins to affect glucose uptake and/or the lowering of plasma glucose levels, as shown herein in the examples.

The proteins, polypeptides, and/or peptides of the invention administered according to this invention may be generated and/or isolated by any means known in the art. The most preferred method for producing the variant is through recombinant DNA methodologies and is well known to those skilled in the art. Such methods are described in Current Protocols in Molecular Biology (John Wiley & Sons, Inc.), which is incorporated herein by reference.

Additionally, the preferred embodiments include a biologically active peptide derived from the variant described herein. Such a peptide will contain at least one of the substitutions described and the variant will possess biological activity. The peptide may be produced by any and all means known to those skilled in the art, examples of which included but are not limited to enzymatic digestion, chemical synthesis or recombinant DNA methodologies.

It is established in the art that fragments of peptides of certain fibroblast growth factors are biologically active. See for example, Baird et al., Proc. Natl. Acad. Sci (USA) 85:2324-2328 (1988), and J. Cell. Phys. Suppl. 5:101-106 (1987). Therefore, the selection of fragments or peptides of the variant is based on criteria known in the art. For example, it is known that dipeptidyl peptidase IV (DPP-IV, or DPP-4) is a serine type protease involved in inactivation of neuropeptides, endocrine peptides, and cytokines (Damme et al. Chem. Immunol. 72: 42-56, (1999)). The N-terminus of FGF21 (HisProllePro) contains two dipeptides that could potentially be substrates to DPP-IV, resulting in a fragment of FGF21 truncated at the N-terminus by 4 amino acids. Unexpectedly, this fragment of wild-type FGF21 has been demonstrated to retain biological activity, thus, proteins of the present invention truncated at the N-terminus by up to 4 amino acids, is an embodiment of the present invention.

The invention also encompasses polynucleotides encoding the above-described variants that may be in the form of RNA or in the form of DNA, which DNA includes cDNA, genomic DNA, and synthetic DNA. The DNA may be double-stranded or single-stranded. The coding sequences that encode the proteins of the present invention may vary as a result of the redundancy or degeneracy of the genetic code.

The polynucleotides that encode for the fusion proteins of the invention may include the following: only the coding sequence for the variant, the coding sequence for the variant and additional coding sequence such as a functional polypeptide, or a leader or secretory sequence or a pro-protein sequence; the coding sequence for the variant and non-coding sequence, such as introns or non-coding sequence 5' and/or 3' of the coding sequence for the variant. Thus the term "polynucleotide encoding a variant" encompasses a polynucleotide that may include not only coding sequence for the variant but also a polynucleotide, which includes additional coding and/or non-coding sequence.

The invention further relates to variants of the described polynucleotides that encode for fragments, analogs and derivatives of the polypeptide that contain the indicated substitutions. The variant of the polynucleotide may be a naturally occurring allelic variant of the human FGF21 sequence, a non-naturally occurring variant, or a truncated variant as described above. Thus, the present invention also includes polynucleotides encoding the variants described above, as well as variants of such polynucleotides, which variants encode for a fragment, derivative or analog of the disclosed variant. Such nucleotide variants include deletion variants, substitution variants, truncated variants, and addition or insertion variants as long as at least one of the indicated amino acid substitutions of the first or second embodiments is present.

The polynucleotides of the invention will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences. The FGF21 variant can be expressed in mammalian cells, insect, yeast, bacterial or other cells under the control of appropriate promoters. Cell free translation systems can also be employed to produce such proteins using RNAs derived from DNA constructs of the present invention.

*E. coli* is a prokaryotic host useful particularly for cloning the polynucleotides of the present invention. Other microbial hosts suitable for use include *Bacillus subtilus, Salmonella typhimurium*, and various species of *Serratia, Pseudomonas, Streptococcus*, and *Staphylococcus*, although others may also be employed as a matter of choice. In these prokaryotic hosts, one can also make expression vectors, which will typically contain expression control sequences compatible with the host cell (e.g., an origin of replication). In addition, any of a number of well-known promoters may be present, such as the lactose promoter system, a tryptophan (Trp) promoter system, a beta-lactamase promoter system, or a promoter system from phages lambda or T7. The promoters will typically control expression, optionally with an operator sequence, and have ribosome binding site sequences and the like, for initiating and completing transcription and translation.

One skilled in the art of expression of proteins will recognize that methionine or methionine-arginine sequence can be introduced at the N-terminus of the mature sequence (SEQ ID NO: 3) for expression in *E. coli* and are contemplated within the context of this invention. Thus, unless otherwise noted, proteins of the present invention expressed in *E. coli* have a methionine sequence introduced at the N-terminus.

Other microbes, such as yeast or fungi, may also be used for expression. *Pichia pastoris, Saccharomyces cerevisiae, Schizosaccharomyces pombe*, and *Pichia angusta* are examples of preferred yeast hosts, with suitable vectors having expression control sequences, such as promoters, including 3-phosphoglycerate kinase or other glycolytic enzymes, and an origin of replication, termination sequences and the like as desired. *Aspergillus niger, Trichoderma reesei*; and *Schizophyllum commune*, are examples of fungi hosts, although others may also be employed as a matter of choice.

Mammalian tissue cell culture may also be used to express and produce the polypeptides of the present invention. Eukaryotic cells are actually preferred, because a number of suitable host cell lines capable of secreting intact variants have been developed in the art, and include the CHO cell lines, various COS cell lines, NSO cells, Syrian Hamster Ovary cell lines, HeLa cells, or human embryonic kidney cell lines (i.e. HEK293, HEK293EBNA).

Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are promoters derived from SV40, adenovirus, bovine papilloma virus, cytomegalovirus, Raus sarcoma virus, and the like. Preferred polyadenylation sites include sequences derived from SV40 and bovine growth hormone.

The vectors containing the polynucleotide sequences of interest (e.g., the fusion proteins of the invention and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Various methods of protein purification may be employed and such methods are known in the art and described, for example, in Deutscher, Methods in Enzymology 182: 83-9 (1990) and Scopes, Protein Purification: Principles and Practice, Springer-Verlag, NY (1982). The purification step(s) selected will depend, for example, on the nature of the production process used for the fusion proteins of the invention.

The proteins, polypeptides, and/or peptides of the invention, e.g., the dual activity fusion proteins of the invention, should be formulated and dosed in a fashion consistent with good medical practice, taking into account the clinical condition of the patient, the site of delivery of the protein compositions, the method of administration, the scheduling of administration, and other factors known to practitioners. The "therapeutically effective amount" of the fusion proteins of the invention for purposes herein is thus determined by such considerations.

The pharmaceutical compositions of the proteins of the present invention may be administered by any means that achieve the generally intended purpose: to treat type 1 and type 2 diabetes mellitus, obesity, metabolic syndrome, or critically ill patients. Non-limiting permissible means of administration include, for example, by inhalation or suppository or to mucosal tissue such as by lavage to vaginal, rectal, urethral, buccal and sublingual tissue, orally, nasally, topically, intranasally, intraperitoneally, parenterally, intravenously, intramuscularly, intrasternally, by intraarticular injection, intralymphatically, interstitially, intra-arterially, subcutaneously, intrasynovial, transepithelial, and transdermally. In some embodiments, the pharmaceutical compositions are administered by lavage, orally or inter-arterially. Other suitable methods of introduction can also include rechargeable or biodegradable devices and slow or sustained release polymeric devices. The pharmaceutical compositions of this invention can also be administered as part of a combinatorial therapy with other known metabolic agents.

The dosage administered will be dependent upon the age, health, and weight of the recipient, kind of concurrent treatment, if any, frequency of treatment, and the nature of the effect desired. Compositions within the scope of the invention include all compositions wherein an FGF21 variant is present in an amount that is effective to achieve the desired medical effect for treatment type 1 or type 2 diabetes mellitus, obesity, or metabolic syndrome. While individual needs may vary from one patient to another, the determination of the optimal ranges of effective amounts of all of the components is within the ability of the clinician of ordinary skill.

The proteins of the present invention can be formulated according to known methods to prepare pharmaceutically useful compositions. A desired formulation would be one that is a stable lyophilized product that is reconstituted with an appropriate diluent or an aqueous solution of high purity with optional pharmaceutically acceptable carriers, preservatives, excipients or stabilizers [Remington's Pharmaceutical Sciences 16th edition (1980)]. The proteins of the present invention may be combined with a pharmaceutically acceptable buffer, and the pH adjusted to provide acceptable stability, and a pH acceptable for administration.

For parenteral administration, in one embodiment, the fusion proteins of the invention are formulated generally by mixing one or more of them at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. Preferably, one or more pharmaceutically acceptable anti-microbial agents may be added. Phenol, m-cresol, and benzyl alcohol are preferred pharmaceutically acceptable anti-microbial agents.

Optionally, one or more pharmaceutically acceptable salts may be added to adjust the ionic strength or tonicity. One or more excipients may be added to further adjust the isotonicity of the formulation. Glycerin, sodium chloride, and mannitol are examples of an isotonicity adjusting excipient.

Those skilled in the art can readily optimize pharmaceutically effective dosages and administration regimens for therapeutic compositions comprising Proteins of the invention, as determined by good medical practice and the clinical condition of the individual patient. A typical dose range for the proteins of the present invention will range from about 0.01 mg per day to about 1000 mg per day (or about 0.05 mg per week to about 5000 mg per week administered once per week) for an adult. Preferably, the dosage ranges from about 0.1 mg per day to about 100 mg per day (or about 0.5 mg per week to about 500 mg per week administered once per week), more preferably from about 1.0 mg/day to about 10 mg/day (or about 5 mg per week to about 50 mg per week administered once per week). Most preferably, the dosage is about 1-5 mg/day (or about 5 mg per week to about 25 mg per week administered once per week). The appropriate dose of an FGF21 variant administered will result in lowering blood glucose levels and increasing energy expenditure by faster and more efficient glucose utilization, and thus is useful for treating type 1 and type 2 diabetes mellitus, obesity and metabolic syndrome.

In addition, because hyperglycemia and insulin resistance are common in critically ill patients given nutritional support, some ICUs administer insulin to treat excessive hyperglycemia in fed critically ill patients. In fact, recent studies document the use of exogenous insulin to maintain blood glucose at a level no higher than 110 mg per deciliter reduced morbidity and mortality among critically ill patients in the surgical intensive care unit, regardless of whether they had a history of diabetes (Van den Berghe et al. N Engl J Med., 345(19):1359, (2001)). Thus, proteins of the present invention are uniquely suited to help restore metabolic stability in metabolically unstable critically ill patients. Proteins of the invention such as those containing variants of FGF21 are unique in that they stimulate glucose uptake and enhances insulin sensitivity but do not induce hypoglycemia.

In another aspect of the present invention, proteins of the invention for use as a medicament for the treatment of obesity, type 1 and type 2 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, metabolic syndrome, acute myocardial infarction, conditions associated with severe inactivating mutations in the insulin receptor, and other metabolic disorders is contemplated.

Site-Specific FGF21 Mutants

In some embodiments, the fusion proteins of the invention include additional FGF21 mutants or FGF21 analogues with unnatural amino acids.

In some embodiments, the fusion proteins of the invention comprise FGF21 agonists with one or more of the following additional modifications of wild-type FGF21:

(i) additional disulfides, unnatural amino acids, or modifications to promote dimerization such as formation of a disulfide at R154C or introduction of a cysteine at another site, or dimerization through a fused Fc domain, or dimer formation through a cross-linker such as a bifunctional PEG;

(ii) fragments of FGF21;

(iii) proteins selected to have FGF21 activity (binding to beta-klotho and binding and activation of the FGFR's); and (iv) an FGF21 mimetic antibody (of various formats such as Fab, unibody, svFc etc.).

In some embodiments, the fusion proteins of the invention comprise one or more of the following linkers: a simple amide bond, short peptides (particularly Ser/Gly repeats), additional residues from the FGF21 translated sequence, or a larger linker up to an entire protein (such as an Fc domain, an HSA-binding helix bundle, HSA, etc.). The two moieties can also be linked by other chemical means, such as through unnatural amino acids or standard chemical linkers (maleimide-Cys, NHS-Lys, click, etc.)

Other embodiments of the invention include but are not limited to the following attachments, for half-life extension: HSA-binding lipid or small molecule or micelle to either the monomeric or a dimeric version of the fusion.

In certain embodiments of the invention, other attachments may be made to proteins, polypeptides, and/or peptides of the invention, to achieve half-life extension and other improved biological properties. They can include attaching PEG-cholesterol conjugates (including micelles and liposomes) to the proteins, polypeptides, and/or peptides of the invention, and/or attaching sugars (glycosylate) to the proteins, polypeptides, and/or peptides of the invention. In still other embodiments, similar techniques are employed to add conjugates of, e.g., polysialic acid (PSA), hydroxyethyl starch (HES), albumin-binding ligands, or carbohydrate shields to proteins, polypeptides, and/or peptides.

The HESylation technique, for example, couples branched hydroxyethylstarch (HES) chains (60 kDa or 100 kDa, highly branched amylopectin fragments from corn starch) to a protein, polypeptides, and/or peptides via reductive alkylation. Polsialation conjugates proteins, polypeptides, and/or peptides of interest with polysialic acid (PSA) polymers in a manner similar to PEGylation. PSA polymers are negatively charged, non-immunogenic polymers that occur naturally in the body and are available in molecular weights of 10-50 kD.

In still other embodiments of the invention, other attachments or modifications may be made to proteins, polypeptides, and/or peptides of the invention, to achieve half-life extension and other improved biological properties. These include the creation of recombinant PEG (rPEG) groups, and their attachment to the proteins, polypeptides, and/or peptides of the invention. As developed by the company Amunix, Inc. The rPEG technology is based on protein sequences with PEG-like properties that are genetically fused to biopharmaceuticals, avoiding the extra chemical conjugation step. rPEGs are extended half-life exenatide constructs that contain a long unstructured tail of hydrophilic amino acids, and which are capable of both increasing a protein or peptide's serum half-life and slowing its rate of absorption, thus reducing the peak-trough ratio significantly. rPEGs have an increased hydrodynamic radius and show an apparent molecular weight that is about 15-fold their actual molecular weight, mimicking the way PEGylation achieves a long serum half-life.

Truncated FGF21 Polypeptides

One embodiment of the present invention is directed to truncated forms of the mature FGF21 polypeptide (SEQ ID NO:3). This embodiment of the present invention arose from an effort to identify truncated FGF21 polypeptides that are capable of providing an activity that is similar, and in some instances superior, to untruncated forms of the mature FGF21 polypeptide.

As used herein, the term "truncated FGF21 polypeptide" refers to an FGF21 polypeptide in which amino acid residues have been removed from the amino-terminal (or N-terminal) end of the FGF21 polypeptide, amino acid residues have been removed from the carboxyl-terminal (or C-terminal) end of the FGF21 polypeptide, or amino acid residues have been removed from both the amino-terminal and carboxyl-terminal ends of the FGF21 polypeptide. The various truncations disclosed herein were prepared as described herein.

The activity of N-terminally truncated FGF21 polypeptides and C-terminally truncated FGF21 polypeptides can be assayed using an in vitro phospho-ERK assay. Specific details of the in vitro assays that can be used to examine the activity of truncated FGF21 polypeptides can be found in the examples.

The activity of the truncated FGF21 polypeptides of the present invention can also be assessed in an in vivo assay, such as ob/ob mice. Generally, to assess the in vivo activity of a truncated FGF21 polypeptide, the truncated FGF21 polypeptide can be administered to a test animal intraperitoneally. After a desired incubation period (e.g., one hour or more), a blood sample can be drawn, and blood glucose levels can be measured.

a. N-Terminal Truncations

In some embodiments of the present invention, N-terminal truncations comprise 1, 2, 3, 4, 5, 6, 7, or 8 amino acid residues from the N-terminal end of the mature FGF21 polypeptide. Truncated FGF21 polypeptides having N-terminal truncations of fewer than 9 amino acid residues retain the ability of the mature FGF21 polypeptide to lower blood glucose in an individual. Accordingly, in particular embodiments, the present invention encompasses truncated forms of the mature FGF21 polypeptide or FGF21 protein variants having N-terminal truncations of 1, 2, 3, 4, 5, 6, 7, or 8 amino acid residues.

b. C-Terminal Truncations

In some embodiments of the present invention, C-terminal truncations comprise 1, 2, 3, 4, 5, 6, 7, 8, 9, 10, 11, or 12 amino acid residues from the C-terminal end of the mature FGF21 polypeptide. Truncated FGF21 polypeptides having C-terminal truncations of fewer than 13 amino acid residues exhibited an efficacy of at least 50% of the efficacy of wild-type FGF21 in an in vitro ELK-luciferase assay (Yie J. et al. FEBS Letts 583:19-24 (2009)), indicating that these FGF21 mutants retain the ability of the mature FGF21 polypeptide to lower blood glucose in an individual. Accordingly, in particular embodiments, the present invention encompasses truncated forms of the mature FGF21 polypeptide or FGF21 protein variants having C-terminal truncations of 1, 2, 3, 4, 5, 6, 7, 8, 9, 10, 11, or 12 amino acid residues.

c. N-Terminal and C-Terminal Truncations

In some embodiments of the present invention, truncated FGF21 polypeptides can have a combination of N-terminal and C-terminal truncations. Truncated FGF21 polypeptides having a combination of N-terminal and C-terminal truncations share the activity of corresponding truncated FGF21 polypeptides having either the N-terminal or C-terminal truncations alone. In other words, truncated FGF21 polypeptides having both N-terminal truncations of fewer than 9 amino acid residues and C-terminal truncations of fewer than 13 amino acid residues possess similar or greater blood glucose-lowering activity as truncated FGF21 polypeptides having N-terminal truncations of fewer than 9 amino acid residues or truncated FGF21 polypeptides having C-terminal truncations of fewer than 13 amino acid residues. Accordingly, in particular embodiments, the present invention encompasses truncated forms of the mature FGF21 polypeptide or FGF21 protein variants having both N-terminal truncations of 1, 2, 3, 4, 5, 6, 7, or 8 amino acid residues and C-terminal truncations of 1, 2, 3, 4, 5, 6, 7, 8, 9, 10, 11, or 12 amino acid residues.

As with all FGF21 variants of the present invention, truncated FGF21 polypeptides can optionally comprise an amino-terminal methionine residue, which can be introduced by directed mutation or as a result of a bacterial expression process.

The truncated FGF21 polypeptides of the present invention can be prepared as described in the examples described herein. Those of ordinary skill in the art, familiar with standard molecular biology techniques, can employ that knowledge, coupled with the instant disclosure, to make and use the truncated FGF21 polypeptides of the present invention. Standard techniques can be used for recombinant DNA, oligonucleotide synthesis, tissue culture, and transformation (e.g., electroporation, lipofection). See, e.g., Sambrook et al., Molecular Cloning: A Laboratory Manual, supra, which is incorporated herein by reference for any purpose. Enzymatic reactions and purification techniques can be performed according to manufacturer's specifications, as commonly accomplished in the art, or as described herein. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses; chemical analyses; pharmaceutical preparation, formulation, and delivery; and treatment of patients.

The truncated FGF21 polypeptides of the present invention can also be fused to another entity, which can impart additional properties to the truncated FGF21 polypeptide. In one embodiment of the present invention, a truncated FGF21 polypeptide can be fused to an IgG constant domain or fragment thereof (e.g., the Fc region), Human Serum Albumin (HSA), or albumin-binding polypeptides. Such fusion can be accomplished using known molecular biological methods and/or the guidance provided herein. The benefits of such fusion polypeptides, as well as methods for making such fusion polypeptides, are discussed in more detail herein.

FGF21 Fusion Proteins

As used herein, the term "FGF21 fusion polypeptide" or "FGF21 fusion protein" refers to a fusion of one or more amino acid residues (such as a heterologous protein or peptide) at the N-terminus or C-terminus of any FGF21 protein variant described herein.

FGF21 fusion proteins can be made by fusing heterologous sequences at either the N-terminus or at the C-terminus of, for example, an FGF21 protein variant, as defined herein. As described herein, a heterologous sequence can be an amino acid sequence or a non-amino acid-containing polymer. Heterologous sequences can be fused either directly to the FGF21 protein variant or via a linker or adapter molecule. A linker or adapter molecule can be one or more amino acid residues (or -mers), e.g., 1, 2, 3, 4, 5, 6, 7, 8, or 9 residues (or -mers), preferably from 10 to 50 amino acid residues (or -mers), e.g., 10, 11, 12, 13, 14, 15, 16, 17, 18, 19, 20, 25, 30, 35, 40, 45, or 50 residues (or -mers), and more preferably from 15 to 35 amino acid residues (or -mers). A linker or adapter molecule can also be designed with a cleavage site for a DNA restriction endonuclease or for a protease to allow for the separation of the fused moieties.

Heterologous peptides and polypeptides include, but are not limited to, an epitope to allow for the detection and/or isolation of an FGF21 protein variant; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; a functional or non-functional antibody, or a heavy or light chain thereof; and a polypeptide which has an activity, such as a therapeutic activity, different from the FGF21 protein variants of the present invention. Also encompassed by the present invention are FGF21 mutants fused to human serum albumin (HSA).

a. Fc Fusions

In one embodiment of the present invention, an FGF21 protein variant is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas a Fab is short-lived (Capon et al., 1989, Nature 337: 525-31). When joined together with a therapeutic protein, an Fc domain can provide longer half-life or incorporate such functions as Fc receptor binding, protein A binding, complement fixation, and perhaps even placental transfer (Capon et al., 1989).

Throughout the disclosure, Fc-FGF21 refers to a fusion protein in which the Fc sequence is fused to the N-terminus of FGF21. Similarly, throughout the disclosure, FGF21-Fc refers to a fusion protein in which the Fc sequence is fused to the C-terminus of FGF21.

Preferred embodiments of the invention are Fc-FGF21 fusion proteins comprising FGF21 variants as defined herein. Particularly preferred embodiments are Fc-FGF21 fusion proteins comprising a modified Fc fragment (e.g., an FcLALA) and FGF21 variants as defined herein.

Fusion protein can be purified, for example, by the use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region can be a naturally occurring Fc region, or can be altered to improve certain qualities, such as therapeutic qualities, circulation time, or reduced aggregation.

Useful modifications of protein therapeutic agents by fusion with the "Fc" domain of an antibody are discussed in detail in PCT Publication No. WO 00/024782. This document discusses linkage to a "vehicle" such as polyethylene glycol (PEG), dextran, or an Fc region.

b. Fusion Protein Linkers

When forming the fusion proteins of the present invention, a linker can, but need not, be employed. When present, the linker's chemical structure may not critical, since it serves primarily as a spacer. The linker can be made up of amino acids linked together by peptide bonds. In some embodiments of the present invention, the linker is made up of from 1 to 20 amino acids linked by peptide bonds, wherein the amino acids are selected from the 20 naturally occurring amino acids. In various embodiments, the 1 to 20 amino acids are selected from the amino acids glycine, serine, alanine, proline, asparagine, glutamine, and lysine. In some embodiments, a linker is made up of a majority of amino acids that are sterically unhindered, such as glycine and alanine. In some embodiments, linkers are polyglycines, polyalanines, combinations of glycine and alanine (such as poly(Gly-Ala)), or combinations of glycine and serine (such as poly(Gly-Ser)). While a linker of 15 amino acid residues has been found to work particularly well for FGF21 fusion proteins, the present invention contemplates linkers of any length or composition.

The linkers described herein are exemplary, and linkers that are much longer and which include other residues are contemplated by the present invention. Non-peptide linkers are also contemplated by the present invention. For example, alkyl linkers such as can be used. These alkyl linkers can further be substituted by any non-sterically hindering group, including, but not limited to, a lower alkyl (e.g., C1-C6), lower acyl, halogen (e.g., Cl, Br), CN, NH2, or phenyl. An exemplary non-peptide linker is a polyethylene glycol linker, wherein the linker has a molecular weight of 100 to 5000 kD, for example, 100 to 500 kD.

Chemically-Modified Fusion Proteins

Chemically modified forms of the fusion proteins described herein, including, e.g., truncated and variant forms of the FGF21 fusions described herein, can be prepared by one skilled in the art, given the disclosures described herein. Such chemically modified Fusion Proteins are altered such that the chemically modified mutant is different from the unmodified mutant, either in the type or location of the molecules naturally attached to the mutant. Chemically modified mutants can include molecules formed by the deletion of one or more naturally-attached chemical groups.

In one embodiment, proteins of the present invention can be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable. Non-water soluble polymers conjugated to proteins of the present invention also form an aspect of the invention.

Exemplary polymers each can be of any molecular weight and can be branched or unbranched. The polymers each typically have an average molecular weight of between about 2 kDa to about 100 kDa (the term "about" indicating that in preparations of a water-soluble polymer, some molecules will weigh more and some less than the stated molecular weight). The average molecular weight of each polymer is preferably between about 5 kDa and about 50 kDa, more preferably between about 12 kDa and about 40 kDa, and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-(C1-C10), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules that can be used to prepare covalently attached FGF21 protein variant multimers. Also encompassed by the present invention are FGF21 mutants covalently attached to polysialic acid.

Polysaccharide polymers are another type of water-soluble polymer that can be used for protein modification. Therefore, the fusion proteins of the invention fused to a polysaccharide polymer form embodiments of the present invention. Dextrans are polysaccharide polymers comprised of individual subunits of glucose predominantly linked by alpha 1-6 linkages. The dextran itself is available in many molecular weight ranges, and is readily available in molecular weights from about 1 kD to about 70 kD. Dextran is a suitable water-soluble polymer for use as a vehicle by itself or in combination with another vehicle (e.g., Fc). See, e.g., International Publication No. WO 96/11953. The use of dextran conjugated to therapeutic or diagnostic immunoglobulins has been reported. See, e.g., European Patent Publication No. 0 315 456, which is hereby incorporated by reference. The present invention also encompasses the use of dextran of about 1 kD to about 20 kD.

In general, chemical modification can be performed under any suitable condition used to react a protein with an activated polymer molecule. Methods for preparing chemically modified polypeptides will generally comprise the steps of: (a) reacting the polypeptide with the activated polymer molecule (such as a reactive ester or aldehyde derivative of the polymer molecule) under conditions whereby a FGF21 protein variant becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment of the present invention, chemically modified FGF21 mutants can have a single polymer molecule moiety at the amino-terminus (see, e.g., U.S. Pat. No. 5,234,784)

In another embodiment of the present invention, Proteins of the invention can be chemically coupled to biotin. The biotin/Proteins of the invention are then allowed to bind to avidin, resulting in tetravalent avidin/biotin/Proteins of the invention. Proteins of the invention can also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that can be alleviated or modulated by the administration of the present chemically modified FGF21 mutants include those described herein for Proteins of the invention. However, the chemically modified FGF21 mutants disclosed herein can have additional activities, enhanced or reduced biological activity, or other characteristics, such as increased or decreased half-life, as compared to unmodified FGF21 mutants.

Therapeutic Compositions of Fusion Proteins and Administration Thereof

The present invention also provides therapeutic compositions comprising one or more of the fusion proteins of the invention described herein and in admixture with a pharmaceutically or physiologically acceptable formulation agent or pharmaceutically acceptable carrier selected for suitability with the mode of administration. The compositions are specifically contemplated in light of, e.g., the identification of fusions proteins exhibiting enhanced properties.

In some embodiments the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington: The Science and Practice of Pharmacy (1995) Alfonso Gennaro, Lippincott, Williams, & Wilkins.

Acceptable formulation materials preferably are nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides; preferably sodium or potassium chloride; or mannitol sorbitol), delivery vehicles, diluents, excipients and/or pharmaceutical adjuvants (see, e.g., Remington's Pharmaceutical Sciences (18th Ed., A. R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage (see, e.g., Remington's Pharmaceutical Sciences, supra). Such compositions can influence the physical state, stability, rate of in vivo release, and rate of in vivo clearance of the fusion protein of the invention.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the present invention, dual function pharmaceutical compositions can be prepared for storage by mixing the selected composition having the desired degree of purity with optional formulation agents (Remington's Pharmaceutical Sciences, supra) in the form of a lyophilized cake or an aqueous solution. Further, the dual function protein product can be formulated as a lyophilizate using appropriate excipients such as sucrose.

The pharmaceutical compositions containing the fusion proteins of the invention can be selected for parenteral delivery. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention can be in the form of a pyrogen-free, parenterally acceptable, aqueous solution comprising the desired dual function protein in a pharmaceutically acceptable vehicle. A particularly suitable vehicle for parenteral injection is sterile distilled water in which a dual function protein is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, a dual function protein of the invention can be formulated as a dry powder for inhalation. Dual function protein inhalation solutions can also be formulated with a propellant for aerosol delivery. In yet another embodiment, solutions can be nebulized. Pulmonary administration is further described in International Publication No. WO 94/20069, which describes the pulmonary delivery of chemically modified proteins.

It is also contemplated that certain formulations can be administered orally. In one embodiment of the present invention, Fusion Proteins of the invention that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the fusion proteins of the invention. Diluents, flavorings, low melting point waxes, vegetable oils, lubricants, suspending agents, tablet disintegrating agents, and binders can also be employed.

Another pharmaceutical composition can involve an effective quantity of the fusion proteins of the invention in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions comprising Fusion Proteins of the invention will be evident to those skilled in the art, including formulations involving Fusion Proteins of the invention in sustained- or controlled-delivery formulations. Techniques for formulating a variety of other sustained- or controlled-delivery means, such as liposome carriers, bio-erodible microparticles or porous beads and depot injections, are also known to those skilled in the art (see, e.g., International Publication No. WO 93/15722, which describes the controlled release of porous polymeric microparticles for the delivery of pharmaceutical compositions, and Wischke & Schwendeman, 2008, Int. J Pharm. 364: 298-327, and Freiberg & Zhu, 2004, Int. J Pharm. 282: 1-18, which discuss microsphere/microparticle preparation and use).

Additional examples of sustained-release preparations include semipermeable polymer matrices in the form of shaped articles, e.g. films, or microcapsules. Sustained release matrices can include polyesters, hydrogels, polylactides (U.S. Pat. No. 3,773,919 and European Patent No. 0 058 481), copolymers of L-glutamic acid and gamma ethyl-L-glutamate (Sidman et al., 1983, Biopolymers 22: 547-56), poly(2-hydroxyethyl-methacrylate) (Langer et al., 1981, J. Biomed. Mater. Res. 15: 167-277 and Langer, 1982, Chem. Tech. 12: 98-105), ethylene vinyl acetate (Langer et al., supra) or poly-D-3-hydroxybutyric acid (European Patent No. 0 133 988). Sustained-release compositions can also include liposomes, which can be prepared by any of several methods known in the art. See, e.g., Epstein et al., 1985, Proc. Natl. Acad. Sci. U.S.A. 82: 3688-92; and European Patent Nos. 0 036 676, 0 088 046, and 0 143 949.

The pharmaceutical compositions of the invention to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

In a specific embodiment, the present invention is directed to kits for producing a single-dose administration unit. The kits can each contain both a first container having a dried protein and a second container having an aqueous formulation. Also included within the scope of this invention are kits containing single and multi-chambered pre-filled syringes (e.g., liquid syringes and lyosyringes).

Dosages of Fusion Proteins and Administration Thereof

The effective amount of an pharmaceutical composition of the invention to be employed therapeutically will depend, for example, upon the therapeutic context and objectives. One skilled in the art will appreciate that the appropriate dosage levels for treatment will thus vary depending, in part, upon the molecule delivered, the indication for which the fusion protein variant is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg.

The frequency of dosing will depend upon the pharmacokinetic parameters of the dual function protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraarterial, intraportal, or intralesional routes; by sustained release systems (which may also be injected); or by implantation devices. Where desired, the compositions can be administered by bolus injection or continuously by infusion, or by implantation device.

Alternatively or additionally, the composition can be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

Therapeutic Uses of Fusion Proteins

Proteins of the invention can be used to treat, diagnose, ameliorate, or prevent a number of diseases, disorders, or conditions, including, but not limited to metabolic disorders. In one embodiment, the metabolic disorder to be treated is diabetes, e.g., type 2 diabetes mellitus. In another embodiment, the metabolic disorder is obesity. Other embodiments include metabolic conditions or disorders such as type 1 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, metabolic syndrome, hypertension, cardiovascular disease, acute myocardial infarction, atherosclerosis, peripheral arterial disease, stroke, heart failure, coronary heart disease, kidney disease, diabetic complications, neuropathy, disorders associated with severe inactivating mutations in the insulin receptor, gastroparesis and other metabolic disorders.

In application, a disorder or condition such as type 1 or type 2 diabetes mellitus or obesity can be treated by administering an FGF21 protein variant as described herein to a patient in need thereof in the amount of a therapeutically effective dose. The administration can be performed as described herein, such as by IV injection, intraperitoneal injection, intramuscular injection, or orally in the form of a tablet or liquid formation. In most situations, a desired dosage can be determined by a clinician, as described herein, and can represent a therapeutically effective dose of the FGF21 mutant polypeptide. It will be apparent to those of skill in the art that a therapeutically effective dose of FGF21 mutant polypeptide will depend, inter alia, upon the administration schedule, the unit dose of antigen administered, whether the nucleic acid molecule or polypeptide is administered in combination with other therapeutic agents, the immune status and the health of the recipient. The term "therapeutically effective dose," as used herein, means that amount of FGF21 mutant polypeptide that elicits the biological or medicinal response in a tissue system, animal, or human being sought by a researcher, medical doctor, or other clinician, which includes alleviation of the symptoms of the disease or disorder being treated.

Having now described the present invention in detail, the same will be more clearly understood by reference to the following examples, which are included herewith for purposes of illustration only and are not intended to be limiting of the invention.

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); and Sambrook et al., Molecular Cloning: A Laboratory Manual (2nd Edition, 1989).

EXAMPLES

Example 1: Preparation of FGF21 Variant Proteins

Expression Construct for FGF21 V76:

The FGF21 variants were cloned into the modified *E. coli* expression vector pET30a, described by Achmuller et al. (2007) (Nature Methods 4:1037-1043), to generate in-frame fusions to a hexa-histidine tag followed by the $N^{pro}$-EDDIE tag at the N-terminus of FGF21 (aa 33-209).

Expression and Purification of FGF21 V76:

The pET30a-His-$N^{pro}$-EDDIE-FGF21 expression plasmid was transformed into *E. coli* BL21 Star (DE3) competent cells (Invitrogen). Overnight growth from a single colony of freshly transformed cells was carried out in 50 mL of Terrific Broth (TB) containing 50 µg/mL of kanamycin at 37° C. The pre-culture was transferred into 1 L of TB medium with kanamycin and cultured in baffled flasks at 37° C. with shaking at 250 rpm. After 6 hour of culture, expression of FGF21 was induced by the addition of IPTG at a final concentration of 1 mM, and the cultures were grown overnight at 37° C. The cells were then harvested and resuspended into 50 mL of ice-cold lysis buffer; 50 mM Tris-HCl, pH 8, 150 mM NaCl, 1 mM EDTA, followed by lysis using a Microfluidizer™.

Inclusion bodies (IBs) were precipitated by centrifugation at 30,000×g for 1 hour at 4° C. The IBs were washed with 50 mM Tris-HCl, pH 8, 150 mM NaCl and then dissolved into 30 mL of dissolving buffer; 10 mM Tris-HCl, pH 8, 100 mM $NaH_2PO_4$, 6 M GnHCl. The dissolved IBs were clarified by centrifugation at 30,000×g for 1 hour at 25° C. The IB solution was loaded onto a 5 mL column of Ni-NTA high performance resin (GE Healthcare) equilibrated with the dissolving buffer. Proteins bound to the resin were eluted by decreasing the pH to 4.5. The eluate was conditioned by adjusting pH and adding dithiothreitol (DTT) at a concentration of 20 mM. The conditioned eluate was slowly diluted into 1 L of refolding buffer; 50 mM Tris-HCl, pH 8, 0.5 M arginine, 20 mM DTT, followed by incubation for 2 days at 4° C. The diluted sample was concentrated and buffer-exchanged into 20 mM Tris-HCl, pH 9 using an ultrafiltration method. The concentrated sample was loaded onto a 10 mL column of Q sepharose fast flow resin (GE Healthcare) equilibrated with 20 mM Tri-HCl (pH 9).

After washing the resin with the equilibration buffer, proteins bound to the resin were eluted with 20 mM Tris-HCl, pH 9, 500 mM NaCl. To remove the cleaved off His-N$^{pro}$ fusion fragment and any uncleaved fusion protein from the refolded FGF21 protein, the eluate was loaded onto a 5 mL column of Ni-NTA high performance resin equilibrated with 20 mM Tris, pH 8.0, 50 mM imidazole, and the flow-through fraction containing FGF21 was collected. To reduce endotoxin levels, the FGF21 fraction was treated with an EndoTrap HD resin (Hyglos) equilibrated with 10 mM Tris, pH 8, 50 mM imidazole, 500 mM NaCl, 1 mM $CaCl_2$. The low-endotoxin sample was dialyzed against PBS and then sterilized with a 0.22 μm filter. The purified FGF21 protein was snap-frozen in liquid nitrogen and stored at −80° C. Protein concentration was determined by absorbance at 280 nm using 9362 M-1 cm-1 as the molar extinction coefficient for FGF21. Protein purity and integrity were determined by HPLC, SDS-PAGE and liquid chromatography-mass spectrometry.

Cysteine PEGylation of FGF21 Variants:

FGF21 Variant V76 (R154C) variant has the tendency to dimerize via the engineered cysteine; therefore, prior to PEGylation the protein solution (typically 5 mg/mL in Tris buffer) was mildly reduced with 5 mM mercaptoethylamine for 30 minutes on ice and immediately desalted in 20 mM Tris, pH 7. The freshly reduced protein (typically 3 mg/mL) was then immediately PEGylated with 1.5 equivalent of 40 kDa branched maleimido-PEG reagent (NOF, Cat. #GL2-400MA from the Sunbright series) for 3 hours on ice. The PEGylated protein was finally purified by anion exchange chromatography (MonoQ) with overall yields of about 25%.

Expression Constructs for Fc-FGF21 Fusion Variants:

The cDNAs for human FGF21 variants encoding amino acids 33-209 were cloned into a mammalian expression vector downstream of the cytomegalovirus (CMV) promoter in-frame with N-terminal sequences including a leader peptide (immunoglobulin kappa-chain) to direct secretion of the proteins, followed by an Fc domain and a short linker.

Expression and Purification of Fc-FGF21 Variants:

The Fc-FGF21 variant proteins were expressed into HEK293T cells (American Type Culture Collection). Cells were grown in suspension culture at 37° C., 8% $CO_2$, in Freestyle 293 Expression Medium (Invitrogen, Cat. #12338-018) until day of transfection. Cells were centrifuged at 1000×g for 7 min in a swinging bucket rotor and counted using an automated cell counter. Cells were diluted in 900 mL of Freestyle 293 media to a final concentration of $1.4 \times 10^6$ cells/mL and placed into a 3 L non-baffled flask (Corning, Cat. #431252). Cells were transfected using a mixture of polyethyleneimine (PEI) and plasmid as follows. Three mL of a sterile 1 mg/mL stock of linear, M.W. 25,000, PEI (Alfa Aesar, Cat. #43896) was added to 50 mL of Freestyle 293 media, mixed gently and incubated at 25° C. for 5 minutes. At the same time, 1 mg of endotoxin-free plasmid was added to 50 mL Freestyle 293 media and sterile filtered using a 0.22 uM filter. The PEI mixture was then added to the sterile filtered DNA, mixed gently and allowed to incubate at 25° C. for 10 minutes. The PEI-plasmid mixture was then added to the 3 L flask containing the diluted HEK 293T cells and placed at in a shaking incubator at 125 RPM, 37° C., 8% $CO_2$.

On day 6 post-transfection, the cells were centrifuged at 2000×g for 10 minutes and the supernatant was harvested. The supernatant was further clarified by filtration through a 0.8/0.2 uM filter (Pall Corporation, Cat. #4628).

Batch purification of the FGF21 protein was done by adding 1 mL of recombinant Protein A Sepharose Fast Flow (GE, Cat. #17-5138-03), per 20 mg of expected protein to be purified, directly to the clarified supernatant and incubating for 1 hour at 4° C. with gentle rotation. The supernatant mixture was then poured over a disposable Poly-Prep Chromatography Column (Bio-Rad, Cat. #731-1550) and the flow through was discarded. The retained beads were washed with 5 column volumes of DPBS, pH 7.4 (Invitrogen, Cat. #14190-144). Elution of the protein from the Protein A beads was done by adding 20 column volumes of 50 mM Sodium Citrate buffer, pH 3.0.

The elution buffer was neutralized by the addition of 20% Tris-HCL buffer, pH 9.0. Size exclusion chromatography was preformed as a secondary polishing step by running the Protein A batch purified material over a High Load 26/600 Superdex 200 pg column (GE, Cat. #28-9893-36). The purified protein yield was quantified by A280. SDS-Page was run to verify purity and molecular weight. Endotoxin level was quantified by using the Endosafe PTS system (Charles River Labs).

Example 2: Measuring FGF21 Dependent 2-Deoxyglucose (2-DOG) Uptake

FGF21 has been shown to stimulate glucose-uptake in mouse 3T3-L1 adipocytes in the presence and absence of insulin, and to decrease fed and fasting blood glucose, triglycerides, and glucagon levels in ob/ob and db/db mice and 8 week old ZDF rats in a dose-dependent manner, thus, providing the basis for the use of FGF21 as a therapy for treating diabetes and obesity (see, e.g., patent publication WO03/011213, and Kharitonenkov et al., (2005) Jour. of Clinical Invest. 115:1627-1635). Also, FGF21 was observed to stimulate tyrosine phosphorylation of FGFR-1 and FGFR-2 in 3T3-L1 adipocytes.

3T3-L1 fibroblasts were purchased from ATCC (Cat. # CL173). The cells were grown to confluency in 150 cm petri-dish and were maintained in DMEM with high glucose (Invitrogen, Cat. #11995065) supplemented with 10% Fetal Bovine Serum and 1% penicillin-streptomycin for an additional 4 days. Cells were then differentiated in the above media supplemented with 4 μg/mL insulin (Sigma, Cat. #I-5500), 115 μg/mL IBMX (Sigma, Cat. #I5879) and 0.0975 μg/mL dexamethasone (Sigma, Cat. #D1756) for 3 days after which the differentiation media was replaced with complete DMEM. One plate of differentiated 3T3-L1 adipocytes were seeded into four 96-well plates the day after medium replacement.

The adipocytes were then treated with FGF21-WT and FGF21 variant protein (see Table 2 for list of variants; 30 pM to 100 nM is the typical concentration range used) overnight in complete medium. The adipocytes treated with FGF21 samples were serum starved in 50 μL per well KRH buffer (0.75% NaCl; 0.038% KCl; 0.0196% $CaCl_2$; 0.032% $MgSO_4$; 0.025M HEPES, pH 7.5; 0.5% BSA; 2 mM sodium pyruvate) for 2 hours. The wells for blank were added with 1 μL (final concentration 5 μg/ml) cytochalasin B for 15 min. [3H]-2-DOG (20.6 mCi/mmoL, 1 mCi/mL) was diluted 1:20 in 5.1 mM cold 2-DOG and 1 μL diluted 2-DOG was added per well and the cells were incubated for 5 min. The cells were washed with 100 μL/well KRH buffer three times. 40 μL/well 1% SDS was added to cells and the cells were shaken for at least 10 minutes. 200 μL/well scintillation fluid was added and the plates were shaken overnight and read in beta-microplate reader. The values obtained from an entire column/row, which were treated with cytochalasin B, was averaged and subtracted from all other values. The data were analyzed by GraphPad Prism software, the results of which are summarized in Table 2. Fc-FGF21 Fusion Variants V101, V103 and V188 are superior to PEGylated FGF21 Variant V76 in for induction of 2-deoxyglucose uptake by mouse 3T3L1 adipocytes.

Example 3: pERK in Cell Western (ICW) Assay

HEK293 cells stably transfected with human β-klotho were cultured in DMEM high glucose, 10% FBS, 1% PS and 600 ng/mL G418 are seeded in poly-D-lysine coated 96-well plates (BD bioscience, Cat. #356640) at 30,000 cells per well overnight. The cells were serum starved in DMEM high glucose, 0.5% BSA and 10 mM HEPES for 4 hours. WT FGF21 and the FGF21 variants (see Table 3 for list of variants) were diluted to various concentrations (100 pM to 300 nM is the typical concentration range used) in starvation medium. The cells were stimulated with FGF21 for 10 minutes. Following FGF21 or FGF21 Variant protein stimulation, the media was aspirated from the wells and the cells were washed once with 100 μL cold PBS and then fixed with 100 μl of 4% formaldehyde for 15 minutes at room temperature and followed by an additional 10 minute incubation with 100 μL ice-cold methanol.

After fixation, the cells were washed with 0.3% Triton X-100 in PBS four times, 5 minutes each. 150 μL Odyssey Blocking Buffer was added to the permeabilized cells at room temperature for 1.5 hours. Phospho-ERK (pERK) antibody was diluted to a concentration of 0.17 μg/mL (1:200 dilution, or the dilutions indicated), and total-ERK (tERK) antibody was diluted to a concentration of 2.2 μg/mL (1:200 dilution, or the dilutions indicated) in Odyssey Blocking Buffer. 50 μL was added to every well, omitting one column which was only treated with secondary antibody to normalize for background. The plate was covered with the wet paper tower and lid to prevent evaporation and then incubated at 4° C. overnight.

Afterwards, the primary antibody was aspirated and the cells were washed four times with 0.3% Tween 20 in PBS for 5 minutes each. During the washing, the secondary antibody reaction mixture was prepared in Odyssey Blocking Buffer containing 1:1000-diluted (or the dilutions indicated) goat anti-mouse Alexa 680 and 1:1000-diluted (or the dilutions indicated) IRDye800 goat anti-rabbit antibody. Once the washing was completed, 40 μL of the reaction mixture was added to each well. Plates were covered with black lid to protect the secondary antibody from light, and plates were incubated at room temperature for 1 hour on a shaker. Finally, the cells were washed again four times with 0.3% Tween 20 in PBS for 5 minutes each and then scanned on the LI-COR Bioscience Odyssey Infrared Imaging System (Li-Cor Biosciences, Lincoln, Nebr.) in the 700 nm (red) and 800 nm (green) channels. Alexa 680 stained the tERK with far-red fluorescence (emission wavelength 668 nm), while IRDye800 stained the pERK with green fluorescence (emission wavelength 800 nm). To eliminate the fluorescent background, the values obtained from an entire column/row, which was treated with only secondary antibody, was averaged and subtracted from all other values obtained from the plate. For normalization of the amount of pERK present in each sample, the values for pERK in each well was divided by the values of tERK. The data were analyzed by GraphPad Prism software, the results of which are summarized in Table 2. Fc-FGF21 Fusion Variants V101, V103 and V188 are superior to PEGylated FGF21 Variant V76 in this ERK phosphorylation assay.

TABLE 2

Summary of ERK in cell Western and Mouse 3T3L1 Adipocyte Glucose Uptake Assay Results

| FGF21 Variant ID | pERK (HEK293/human β-klotho) EC50 ± SEM | Glucose Uptake (Mouse 3T3L1 adipocytes) EC50 ± SEM |
|---|---|---|
| V76 | 13 ± 4 nM (n = 5) | 5 ± 1 nM (n = 3) |
| V101 | 0.60 ± 0.06 nM (n = 5) | 0.60 ± 0.06 nM (n = 3) |
| V103 | 0.9 ± 0.3 nM (n = 5) | 0.60 ± 0.07 nM (n = 3) |
| V188 | 0.4 ± 0.1 nM (n = 3) | 0.48 ± 0.14 nM (n = 3) |

Example 4: In Vivo Tests of FGF21 Variants

The ob/ob mouse is a mouse model for type 2 diabetes. The mice lack functional leptin and are characterized by hyperglycemia, insulin resistance, hyperphagia, hepatic steatosis and obesity. Male ob/ob mice (10-13 weeks old) were used to measure the effect on blood glucose of the following PEGylated FGF21 variant V76 and Fc-FGF21 fusion variants V101, V103 and V188.

FGF21 variants or PBS vehicle were administered s.c. at 1 mg/kg (V101, V103 and V188) or s.c at 5 mg/kg V76 twice per week 12 days (4 doses total). On the first day of the study, tail blood glucose and body weight were measured and mice were allocated into different groups (n=8 per group) with mean glucose and body weight matched among the groups. Blood glucose was measured using a glucometer (OneTouch). Plasma insulin was measured on day 1 before dosing and on day 12, 24 hours post the last dose. The results of these studies are summarized in Table 5.

The results of these studies are summarized in Table 3 and FIGS. 1-3. Fc-FGF21 Fusion Variants V101, V103 and V188 are superior to PEGylated FGF21 Variant V76 on every endpoint measured in these studies and at a five-fold lower dose.

TABLE 3

% changes versus vehicle in plasma glucose, insulin, body weight (BW) gain, liver TG/lipid by FGF21 variants during 12-day studies in ob/ob mice.
Summary of 12-day treatment study in diabetic ob/ob mice (% change from vehicle)

| FGF21 Variant ID | Dose (mg/kg) | Total Glucose (AUC) | Plasma Insulin | Body Weight | Liver lipid |
|---|---|---|---|---|---|
| V76 | 5.0 | −42% | −46% | −7% | −30% |
| V101 | 1.0 | −53% | −82% | −12% | −44% |
| V103 | 1.0 | −46% | −69% | −12% | −50% |
| V188 | 1.0 | −42% | −59% | −11% | −51% |

Example 5: Pharmacokinetics of FGF21 Fusion Variants in Mice

To determine the pharmacokinetic profile of Fc-FGF21 Fusion Variants V101, V103 and V188, C57BL/6J mice were injected IV with 1 mg/kg test article and bled at various time points out to 16 days (384 hours). Blood samples were collected into EDTA-coated microtainer tubes from either the submandibular or retro-orbital plexus. Approximately 50 µL of blood was collected at each time point, yielding ~25 µL of plasma.

Figure 4A:
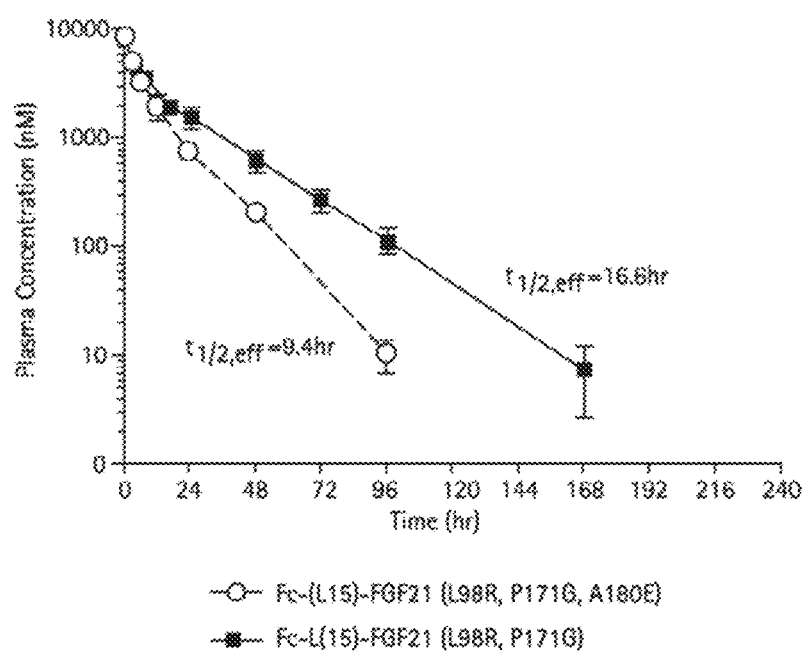
FIGS. 4A-4D demonstrate the superior pharmacokinetic and thermodynamic properties possessed by the fusion proteins of the invention over FGF21 fusion proteins in the art.
Figure 4B:
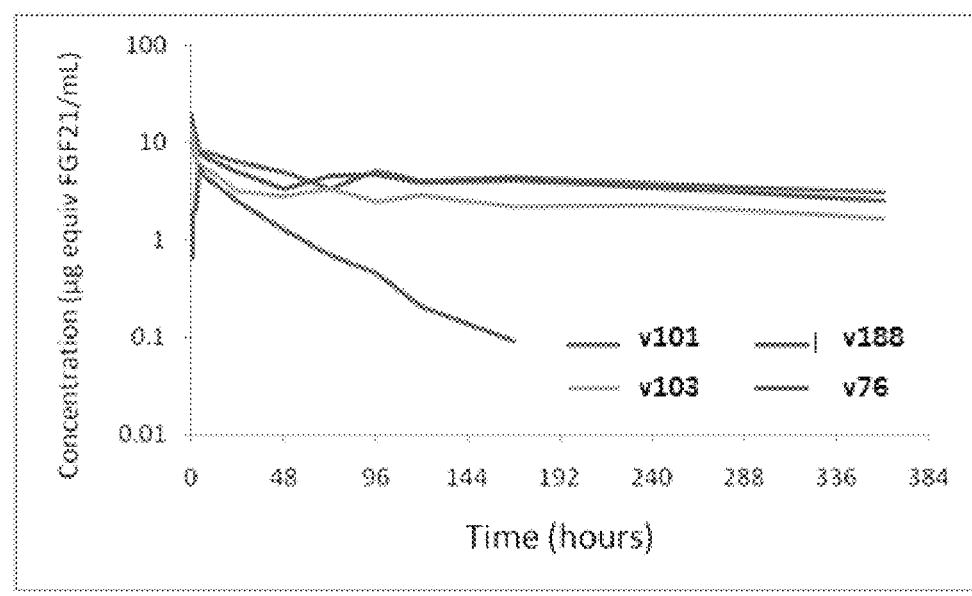

To measure plasma concentrations of test articles by ELISA, 384-well plates were coated overnight at room temperature (RT) with 2 µg/mL of anti-Human Fc-gamma goat polyclonal antibody (30 µL/well) and then blocked with a casein-based diluent for 2 hour at RT (100 µL/well). Diluted samples, standards, and controls were added to the plate (30 µL/well) and incubated for 2 hour at RT. After the samples were removed, the wells were washed 3 times with a phosphate-based wash solution (100 µL/well). The detection antibody, an HRP-labeled version of the capture antibody, was added to the plate and incubated for 1 hour at RT (30 µL/well). After the plate was again washed 3 times with a phosphate-based wash solution (100 µL/well), a chemiluminescent substrate was added (30 µL/well) and the plate luminescence was read within 5 minutes using an appropriate plate reader. As shown in FIGS. 4A and 4B the Fc-FGF21 fusion variants had a greatly extended plasma half-life relative to known Fc-FGF21 fusions in the art (FIG. 4A) and relative to PEGylated FGF21 variant V76 (FIG. 4B).

Figure 4C:
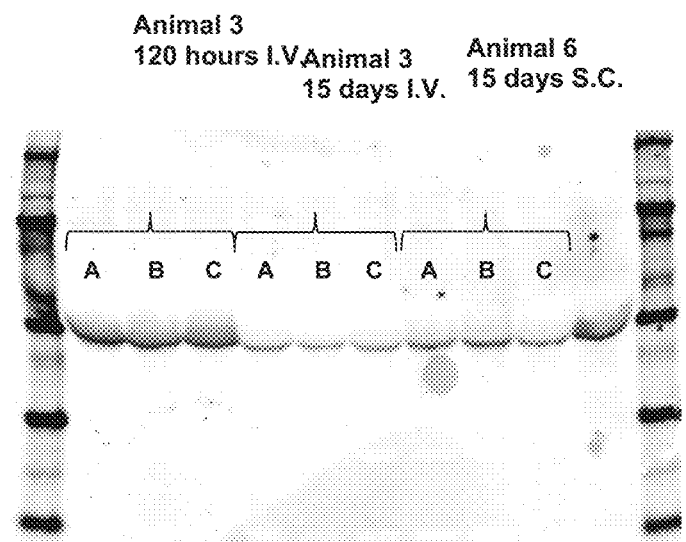
Figure 4D:
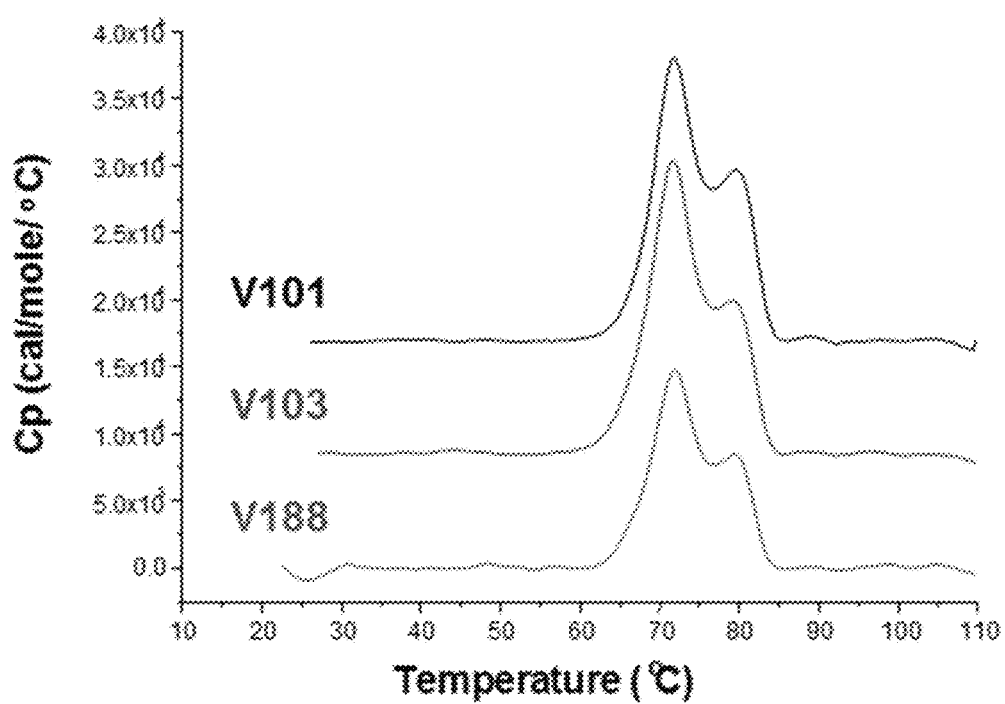

Serum levels of Fc-FGF21 test articles were validated by Western blot for comparison to levels measured by ELISA to ensure that full length Fc-FGF21 variant and not Fc alone was being detected in the ELISA. Two uL of mouse serum was combined with 2.5 uL of 4× loading buffer, 1 uL of 10× denaturant and 4 uL of dH$_2$O, heated to 95° C. for 5 minutes and loaded onto a 4-12% gradient polyacrylamide gel and electrophoresed for 1 hour at 100 Volts (constant voltage). Samples were transferred to nitrocellulose filter paper by Western blot using the iblot system (Invitrogen, Cat. #IB1001, 7 minute run time). The nitrocellulose filters were blocked with 30 mL of Rockland blocking solution (Cat. #MB-070), probed following the snap iblot system protocol with a goat anti-FGF21 primary antibody at a 1:2000 dilution (R&D systems, Cat. #BAF2539) and fluorescently labeled streptavidin as a secondary at a 1:10000 dilution (Licor, Cat. #926-68031). Protein levels were imaged on the Licor Odyssey system at 700 nm and compared with 2 nM control V101 run on the same gel. As shown in FIG. 4C full-length Fc-FGF21 variants V101, V103 and V188 are detectable using on a Western Blot using anti-FGF21 antibody out to 15 days from mouse serum from the pharmacokinetic study.

Example 6: Fc-FGF21 Fusion Variants V101, V103 and V188 are Extremely Thermodynamically Stabile Proteins can be unfolded at specific temperature range. The temperature of protein unfolding is an intrinsic parameter to describe thermal stability of proteins. Differential Scanning calorimetry (DSC) is used to detect the unfolding temperature of protein. This characteristic temperature is described as melting temperature (Tm), which is the peak temperature during protein unfolding.

Original protein samples are diluted in PBS to a concentration of ~1 mg/ml (0.5 mg/ml to 1.2 mg/ml) for a total volume of 0.5 ml. An aliquot of 0.4 ml per well diluted protein sample, standard, PBS, and DI water are added to DSC 96-well plate. The plate is then covered by a seal. Samples were analyzed in a 96 well Differential Scanning calorimeter from MicroCal. The temperature was scanned from 10-110 degrees C. at a rate of 1 degree per minute.

As shown in FIG. 4 D the melting temperatures of FGF21 variants V101, V103 and V188 are extremely high. This is in contrast to the lower melting temperatures of FGF21 variant V76 and wild-type FGF21 (not shown). We attribute the improved stability of V101, V103 and V188 to the specific addition of a second disulfide bond from the novel Q55C and G148C mutations. This type of thermodynamic stability is known to protect proteins from proteolysis and can in addition translate into significantly prolonged stability in vivo and the improved pharmacokinetic profiles exemplified by the data in FIGS. 4B and 4C.

What is claimed is:

1. A nucleic acid coding for a fusion protein comprising a fibroblast growth factor 21 (FGF21) variant and an Fc region, wherein the FGF21 variant comprises an amino acid sequence with at least 95% identity to the full length hFGF21 sequence SEQ ID NO:1, and comprises at least the following mutations relative to SEQ ID NO:1: Q55C, G148C, K150R, P158S, S195A, P199G, and G202A, and one of R105K and A109T.

2. A vector comprising the nucleic acid according to claim 1.

3. A host cell comprising the vector of claim 2.

4. A method of producing a fusion protein, wherein the method comprises culturing the host cell of claim 3.

5. The nucleic acid of claim 1, wherein the nucleic acid codes for a fusion protein comprising the amino acid sequence of SEQ ID NO: 10, 11, 12, or 13.

6. A vector comprising the nucleic acid according to claim 5.

7. A host cell comprising the vector of claim 6.

8. A method of producing a fusion protein, wherein the method comprises culturing the host cell of claim 7.

9. The nucleic acid of claim 1, wherein the nucleic acid codes for a fusion protein comprising the amino acid sequence of SEQ ID NO: 11.

10. A vector comprising the nucleic acid according to claim 9.

11. A host cell comprising the vector of claim 10.

12. A method of producing a fusion protein, wherein the method comprises culturing the host cell of claim 11.

* * * * *